(12) United States Patent
Al Atari Abouasi et al.

(10) Patent No.: US 10,925,997 B2
(45) Date of Patent: Feb. 23, 2021

(54) BONE BIOACTIVE COMPOSITION AND USES THEREOF

(71) Applicant: BIOINTELLIGENCE SYSTEMS S.L., Barcelona (ES)

(72) Inventors: Maher Al Atari Abouasi, Barcelona (ES); José Luis Calvo Guirado, Guadalupe (ES)

(73) Assignee: BIOINTELLIGENCE SYSTEMS S.L., Barcelona (ES)

(*) Notice: Subject to any disclaimer, the term of this patent is extended or adjusted under 35 U.S.C. 154(b) by 1 day.

(21) Appl. No.: 16/344,322

(22) PCT Filed: Oct. 26, 2017

(86) PCT No.: PCT/EP2017/077505
§ 371 (c)(1),
(2) Date: Apr. 23, 2019

(87) PCT Pub. No.: WO2018/078044
PCT Pub. Date: May 3, 2018

(65) Prior Publication Data
US 2019/0262499 A1    Aug. 29, 2019

(30) Foreign Application Priority Data

Oct. 26, 2016   (EP) .................................... 16195718
Sep. 26, 2017   (EP) .................................... 17382638

(51) Int. Cl.
| | | |
|---|---|---|
| *A61K 31/00* | (2006.01) | |
| *A61K 45/00* | (2006.01) | |
| *A61K 45/06* | (2006.01) | |
| *A61K 33/00* | (2006.01) | |
| *A61K 33/42* | (2006.01) | |
| *A61L 27/12* | (2006.01) | |
| *A61L 27/46* | (2006.01) | |
| *A61L 27/36* | (2006.01) | |
| *A61C 8/02* | (2006.01) | |
| *A61K 33/14* | (2006.01) | |
| *A61L 27/02* | (2006.01) | |
| *A61L 27/38* | (2006.01) | |
| *A61L 27/50* | (2006.01) | |
| *A61L 27/32* | (2006.01) | |
| *A61K 6/70* | (2020.01) | |

(52) U.S. Cl.
CPC ............ *A61L 27/12* (2013.01); *A61C 8/0006* (2013.01); *A61K 6/70* (2020.01); *A61K 33/14* (2013.01); *A61K 33/42* (2013.01); *A61L 27/025* (2013.01); *A61L 27/32* (2013.01); *A61L 27/38* (2013.01); *A61L 27/50* (2013.01); *A61L 2430/02* (2013.01); *A61L 2430/12* (2013.01)

(58) Field of Classification Search
CPC .... A61K 2300/00; A61K 31/66; A61K 33/42; A61L 2430/02; A61L 27/46; A61L 27/365; A61L 2430/12; A61L 2300/412; A61L 2300/112
See application file for complete search history.

(56) References Cited

U.S. PATENT DOCUMENTS

| | | | | |
|---|---|---|---|---|
| 4,994,237 A | * | 2/1991 | Login | ...................... A01N 1/02 |
| | | | | 435/1.1 |
| 5,217,954 A | * | 6/1993 | Foster | .................. C07K 14/503 |
| | | | | 514/9.1 |
| 5,656,598 A | * | 8/1997 | Dunstan | .................... A61P 5/00 |
| | | | | 514/9.1 |
| 2007/0213832 A1 | | 9/2007 | Wen | |
| 2008/0020349 A1 | * | 1/2008 | Dricot | ................... A61L 27/306 |
| | | | | 433/174 |
| 2014/0363413 A1 | * | 12/2014 | Bourgeaux | .............. A61P 35/04 |
| | | | | 424/93.73 |
| 2015/0119358 A1 | * | 4/2015 | Medina | .................... A61L 27/52 |
| | | | | 514/55 |

FOREIGN PATENT DOCUMENTS

WO    WO-2014020446 A2 *  2/2014   ............. A61L 27/32

OTHER PUBLICATIONS

Lane, Courtney. Phosphate Buffered Saline (PBS) Preparation. Jun. 12, 2015. <https://benchling.com/protocols/EQdKGRCz/phosphate-buffered-saline-pbs-preparation>. (Year: 2015).*
Chazotte, Brad. Mounting Live Cells onto Microscope Slides. 2011. Cold Spring Harbor Laboratory Press. (Year: 2011).*
Kuhlmann, Wolf D. Buffer Solutions. Oct. 9, 2006. (Year: 2006).*
International Search Report dated Feb. 2, 2018 for PCT/EP2017/077505, 5 pages.
Written Opinion of the International Searching Authority dated Feb. 2, 2018 for PCT/EP2017/077505, 7 pages.
Albrektsson, et al., "Osseointegrated Titanium Implants Requirements for ensuring a long-lasting, direct bone-to-implant anchorage in man" Acta Orthop Scand 1981, vol. 52, pp. 155-170.
Anonymous, "Phosphate-buffered saline", https://en.wikipedia.org/wiki/Phosphate-buffered_Saline#cite_note-1, retrieved Apr. 8, 2016.
Anselme, K., "Osteoblast adhesion on biomaterials" Biomaterials 2000, vol. 21, pp. 667-681.
Galler, et al., "Bioengineering of dental stem cells in a PEGylated fibrin gel", Regen Med. 2011, vol. 6, No. 2, pp. 191-200.

(Continued)

*Primary Examiner* — Tracy Liu
(74) *Attorney, Agent, or Firm* — Squire Patton Boggs (US) LLP

(57) ABSTRACT

A bone bioactive composition and kits comprising the composition, means for applying it and/or a metal implant are provided. The bone bioactive composition comprises a water-based salt solution comprising sodium dihydrogen phosphate and sodium chloride, and may also comprise additional elements. The composition and the kits are useful for promoting osteogenesis, particularly when a metal implant is used but also in case of periodontal diseases.

20 Claims, 15 Drawing Sheets
Specification includes a Sequence Listing.

(56) References Cited

OTHER PUBLICATIONS

García, A.J., "Get a grip: integrins in cell-biomaterial interactions", Biomaterials 2005, vol. 26, pp. 7525-7529.
Howlett, et al., "Mechanism of initial attachment of cells derived from human bone to commonly used prosthetic materials during cell culture", Biomaterials1994, vol. 15, No. 3., pp. 213-222.
Kilpadi, et al. "Hydroxylapatite binds more serum proteins, purified integrins, and osteoblast precursor cells than titanium or steel", Journal Biomed Mater Res 2001, vol. 57, pp. 258-267.
Lindahl C., "Biomimetic deposition of hydroxyapatite on titanium implant materials", Uppsala Universitet, Jan. 1, 2012, pp. 978-991.
Lindberg, et al., "Hydrohylapatite growth onf single crystal rutile substrates", Biomaterials, Aug. 1, 2008, vol. 29, No. 23, pp. 3317-3323.
Mohan, et al., "Bone growth factors", Clin Orthop Relat Res 1991,vol. 263, pp. 30-48.
Scotchford, et al., "Chemically patterned, metal-oxide-based surfaces produced by photolithographic techniques for studying protein- and cell-interactions. II: Protein adsorption and early cell interactions", Biomaterials 2003, vol. 24, pp. 1147-1158.
Sheikh, et al., "Natural graft tissues and synthetic biomaterials for periodontal and alveolar bone reconstructive applications: a review", Biomaterials Research 2017, vol. 21, No. 9, pp. 1-20.
Steele, et al., "Attachment of human bone cells to tissue culture polystyrene and to unmodified polystyrene: the effect of surface chemistry upon initial cell attachment", J Biomater Sci Polym Edn 1993, vol. 5, No. 3, pp. 245-257.
Urist, et al., "Bone cell differentiation and growth factors", Science 1983, vol. 220, pp. 680-686.
Wozney, et al., "Growth factors influencing bone development", J Cell Sci Suppl 1990, vol. 13, pp. 149-156.
Yang, et al., "Effects of oestrogen deficiency on rat mandibular and tibial microarchitecture", Dentomaxillofacial Radiology, Jul. 2003, vol. 32, No. 4, pp. 247-251.

* cited by examiner

GROUP A: NO TREATED SURFACE.

15 DAYS

30 DAYS

45 DAYS

60 DAYS

Group C: Treated Surface 2 Implant

15 DAYS

30 DAYS

45 DAYS

60 DAYS

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence

```
<220> FEATURE:
<223> OTHER INFORMATION: Forward primer ALP_1

<400> SEQUENCE: 1
ggacatgcag tacgagctga                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer ALP_1

<400> SEQUENCE: 2
gtcaattctg cctccttcca                                              20

<210> SEQ ID NO 3
<211> LENGTH: 21
<212> TYPE: DNA
<213> ORGANISM: Artificial Sequence
<220> FEATURE:
<223> OTHER INFORMATION: Forward primer ALP_2

<400> SEQUENCE: 3
ccgtggcaac tctatctttg g                                            21

<210> SEQ ID NO 4
<211> LENGTH: 20
<212> TYPE: DNA
<213> ORGANISM: Artificial Sequence
<220> FEATURE:
<223> OTHER INFORMATION: Reverse primer ALP_2

<400> SEQUENCE: 4
gccatacagg atggcagtga                                              20

<210> SEQ ID NO 5
<211> LENGTH: 20
<212> TYPE: DNA
<213> ORGANISM: Artificial Sequence
<220> FEATURE:
<223> OTHER INFORMATION: Forward primer COL1_1

<400> SEQUENCE: 5
actggtgaga cctgcgtgta                                              20

<210> SEQ ID NO 6
<211> LENGTH: 19
<212> TYPE: DNA
<213> ORGANISM: Artificial Sequence
<220> FEATURE:
<223> OTHER INFORMATION: Reverse primer COL1_1

<400> SEQUENCE: 6
cagtctgctg gtccatgta                                               19

<210> SEQ ID NO 7
<211> LENGTH: 22
<212> TYPE: DNA
<213> ORGANISM: Artificial Sequence
<220> FEATURE:
<223> OTHER INFORMATION: Forward primer COL1_2

<400> SEQUENCE: 7
ccctggaaag aatggagatg at                                           22
```

```
<210> SEQ ID NO 8
<211> LENGTH: 23
<212> TYPE: DNA
<213> ORGANISM: Artificial Sequence
<220> FEATURE:
<223> OTHER INFORMATION: Reverse primer COL1_2

<400> SEQUENCE: 8
actgaaacct ctgtgtccct tca                                              23

<210> SEQ ID NO 9
<211> LENGTH: 19
<212> TYPE: DNA
<213> ORGANISM: Artificial Sequence
<220> FEATURE:
<223> OTHER INFORMATION: Forward primer OC_1

<400> SEQUENCE: 9
gtgcagcctt tgtgtccaa                                                   19

<210> SEQ ID NO 10
<211> LENGTH: 19
<212> TYPE: DNA
<213> ORGANISM: Artificial Sequence
<220> FEATURE:
<223> OTHER INFORMATION: Reverse primer OC_1

<400> SEQUENCE: 10
gctcacacac ctccctcct                                                   19

<210> SEQ ID NO 11
<211> LENGTH: 20
<212> TYPE: DNA
<213> ORGANISM: Artificial Sequence
<220> FEATURE:
<223> OTHER INFORMATION: Forward primer OC_2

<400> SEQUENCE: 11
aagagaccca ggcgctacct                                                  20

<210> SEQ ID NO 12
<211> LENGTH: 21
<212> TYPE: DNA
<213> ORGANISM: Artificial Sequence
<220> FEATURE:
<223> OTHER INFORMATION: Reverse primer OC_2

<400> SEQUENCE: 12
aactcgtcac agtccggatt g                                                21

<210> SEQ ID NO 13
<211> LENGTH: 20
<212> TYPE: DNA
<213> ORGANISM: Artificial Sequence
<220> FEATURE:
<223> OTHER INFORMATION: Forward primer RUNX2_1

<400> SEQUENCE: 13
ttactgtcat ggcgggtaac                                                  20

<210> SEQ ID NO 14
<211> LENGTH: 19
<212> TYPE: DNA
<213> ORGANISM: Artificial Sequence
<220> FEATURE:
<223> OTHER INFORMATION: Reverse primer RUNX"_1
```

<400> SEQUENCE: 14
ggttcccgag gtccatcta                                              19

<210> SEQ ID NO 15
<211> LENGTH: 23
<212> TYPE: DNA
<213> ORGANISM: Artificial Sequence
<220> FEATURE:
<223> OTHER INFORMATION: Forward primer RUNX2_2

<400> SEQUENCE: 15
agcaaggttc aacgatctga gat                                         23

<210> SEQ ID NO 16
<211> LENGTH: 23
<212> TYPE: DNA
<213> ORGANISM: Artificial Sequence
<220> FEATURE:
<223> OTHER INFORMATION: Reverse primer RUNX2_2

<400> SEQUENCE: 16
tttgtgaaga cggttatggt caa                                         23

<210> SEQ ID NO 17
<211> LENGTH: 20
<212> TYPE: DNA
<213> ORGANISM: Artificial Sequence
<220> FEATURE:
<223> OTHER INFORMATION: Forward primer ITGa4

<400> SEQUENCE: 17
tccgagtcaa tgtccacaga                                             20

<210> SEQ ID NO 18
<211> LENGTH: 20
<212> TYPE: DNA
<213> ORGANISM: Artificial Sequence
<220> FEATURE:
<223> OTHER INFORMATION: Reverse primer ITGa4

<400> SEQUENCE: 18
gctgggctac cctattcctc                                             20

<210> SEQ ID NO 19
<211> LENGTH: 25
<212> TYPE: DNA
<213> ORGANISM: Artificial Sequence
<220> FEATURE:
<223> OTHER INFORMATION: Forward primer GAPDH

<400> SEQUENCE: 19
ctggtaaagt ggatattgtt gccat                                       25

<210> SEQ ID NO 20
<211> LENGTH: 26
<212> TYPE: DNA
<213> ORGANISM: Artificial Sequence
<220> FEATURE:
<223> OTHER INFORMATION: Reverse primer GAPDH

<400> SEQUENCE: 20
tggaatcata ttggaacatg taaacc                                      26

```
<210> SEQ ID NO 21
<211> LENGTH: 20
<212> TYPE: DNA
<213> ORGANISM: Artificial Sequence
<220> FEATURE:
<223> OTHER INFORMATION: Forward primer BMP2

<400> SEQUENCE: 21
gcggaaacgc cttaagtcca                                               20

<210> SEQ ID NO 22
<211> LENGTH: 20
<212> TYPE: DNA
<213> ORGANISM: Artificial Sequence
<220> FEATURE:
<223> OTHER INFORMATION: Reverse primer BMP2

<400> SEQUENCE: 22
gtggagttca gatgatcagc                                               20

<210> SEQ ID NO 23
<211> LENGTH: 20
<212> TYPE: DNA
<213> ORGANISM: Artificial Sequence
<220> FEATURE:
<223> OTHER INFORMATION: Forward primer OCN

<400> SEQUENCE: 23
gcagacctga catccagtac                                               20

<210> SEQ ID NO 24
<211> LENGTH: 20
<212> TYPE: DNA
<213> ORGANISM: Artificial Sequence
<220> FEATURE:
<223> OTHER INFORMATION: Reverse primer OCN

<400> SEQUENCE: 24
taatctggac tgcttgtggc                                               20
```

BONE BIOACTIVE COMPOSITION AND USES THEREOF

FIELD OF THE INVENTION

The present invention refers to the field of biomedicine and particularly, to compositions for use in promoting osteogenesis. Specifically, the present invention includes compositions for regeneration of dental bone tissue when an implant is used and/or in case of periodontal diseases.

BACKGROUND ART

One of the major problems that the field of implants faces is the failure of the appropriate engraftment of the implant in the bone, leading to the loss of the implant. In order to reduce implant failure, several modifications of specific surface properties such as structure, chemistry, surface charge and wettability have been investigated to improve protein binding and osteointegration of titanium implants (Albrektsson T, et al. "Osseointegrated titanium implants Requirements for ensuring a long-lasting, direct bone-to-implant anchorage in man" Acta Orthop Scand 1981, 52:155-170).

Some peptides and proteins, including collagen and fibronectin, have been used to improve the bioactivity of materials. Both proteins are part of extracellular matrix proteins and have been proven to promote cell adhesion to substrates (Mohan S, et al. "Bone growth factors" Clin Orthop Relat Res 1991, 263:30-48). For most cell types, including connective tissue cells such as osteoblasts and their precursors, adhesion to extracellular matrix is essential for survival (Urist M R, et al. "Bone cell differentiation and growth factors" Science 1983, 220:680-686; Wozney J M, et al. "Growth factors influencing bone development" J Cell Sci Suppl 1990, 13:149-156; Anselme K "Osteoblast adhesion on biomaterials" Biomaterials 2000, 21:667).

In addition, it was previously demonstrated that the negative net charge of the alloy's surface oxide enhanced the protein's intrinsic capacity to bind to osteogenic cell integrin receptors and promote cell spreading (Anselme K "Osteoblast adhesion on biomaterials" Biomaterials 2000, 21:667; Scotchford C A, et al. "Chemically patterned, metal-oxide-based surfaces produced by photolithographic techniques for studying protein- and cell-interactions. II: Protein adsorption and early cell interactions" Biomaterials 2003, 24:1147; Steele J G, et al. "Attachment of human bone cells to tissue culture polystyrene and to unmodified polystyrene: the effect of surface chemistry upon initial cell attachment" J Biomater Sci Polym Ed 1993, 5:245; Howlett C R, et al. "Mechanism of initial attachment of cells derived from human bone to commonly used prosthetic materials during cell culture" Biomaterials 1994, 15:213; Kilpadi K L, et al. "Hydroxylapatite binds more serum proteins, purified integrins, and osteoblast precursor cells than titanium or steel" J Biomed Mater Res 2001, 57:258; García AJ "Get a grip: integrins in cell-biomaterial interactions" Biomaterials 2005, 26:7525).

US20070213832 (Wen Hai B) describes a calcium phosphate implant that is immersed in HBSS (Hank's Buffered salt Solution) or common PBS for 5 days, rinsed with distilled water and then dried in air for 24 hours, resulting in the microscopic observation of a nanoporous mineral layer. The document does not describe any biological effect derived from the above process. The mineral layer is used as delivery vehicle for bioactive compositions. In this sense, the document discloses that an osteogenic capacity can be achieved by incorporating into the mineral layer bioactive agents such as growth factors. Thus, the osteogenic effect is not linked to the mineral layer itself or to the use of the PBS composition, but to the bioactive agents incorporated into the mineral layer.

Lindahl C, 2012 describes a method to form an apatite-like surface on Titanium substrates to mimic the natural bone, comprising the step of immersing the Titanium substrate into PBS or SBF (Simulated body fluid—Kokubo) normally at 37° C. for a period of days to weeks, drying and sterilizing. The result is an apatite-like surface which can be further modified or functionalized to improve the properties of the implant coating, e.g. by incorporation of bone promoting drugs like biphosphonate (Lindahl C. "Biomimetic deposition of hydroxyapatite on titanium implant materials" Uppsala Univ. 1 Jan. 2012, pages 978-91).

Similarly, Lindberg F et al., 2008 describes a method to form an apatite-like surface on titanium material, comprising soaking in PBS solution preheated to 37° C. from 1 to 4 weeks, rinsing with deionized water and drying in air. After this process, precipitated hydroxyapatite can be observed by XRD (Lindberg F. et al., "Hydrohylapatite growth onf single crystal rutile substrates" Biomaterials, Elsevier Science Publishers BV, Barking G B, vol. 29, no 23, 1 Aug. 2008 pages 3317-23)

In addition, another major problem faced in odontology is the treatment and prevention of peri-implantitis and peri-odontitis. Peri-implantitis is defined as a destructive inflammatory process affecting the soft and hard tissues surrounding dental implants produced or induced by bacteria colonizing dental implants and their surroundings. On its side, periodontitis is characterized by the destruction of connective tissue and dental bone support following an inflammatory host response secondary to infection by peri-odontal bacteria. Both diseases are currently treated with antibiotics and with increased or improved dental hygiene. Nevertheless, they still lead sometimes to the loss of the implant or the tooth and/or severe damages in the surrounding tissue (connective tissue and dental bone).

Hence, there remains the need to provide means to avoid implant failure, and thus, promoting a properly engraftment of the implant, more specifically, with dental implants which are commonly titanium implants. In addition, as stated above, there also remains the need to find compositions for use in the treatment or prevention of the periodontal diseases with loss of bone tissue such as periodontitis and peri-implantitis.

SUMMARY OF THE INVENTION

One problem to be solved by the present invention may be seen as related to the provision of means capable of avoiding implant failure and promoting properly engraftment of the implant with the surrounding tissues, specifically when dental implants are used.

The solution is based on the provision of compositions and kits that have been surprisingly found that promote osteogenesis. Specifically, they promote, increase, and accelerate the osteogenesis of the surrounding bone tissue of the implant, thus, regenerating or remodeling bone tissue, promoting implant engraftment and avoiding implant loss.

Since the compositions and kits of the invention promote osteogenesis by theirselves, they are also useful in the treatment of periodontal diseases with loss of bone tissue such as periodontitis and peri-implantitis.

Accordingly, a first aspect of the invention relates to a bone bioactive composition comprising a water-based salt solution comprising sodium dihydrogen phosphate and sodium chloride, for use in promoting osteogenesis.

The term "bone bioactive composition" means that the composition is active or reactive with the bone tissue; i.e. that has an effect on, interacts with, or elicits a response from the bone tissue. In other words, that means that the composition interacts and reacts with the bone tissue in some extension. The maximum extension of this "bioactivity" or reaction would be the bone repair. The term "bioactive" is usually used in the field of implants and prosthetics; for example, "bioactive glasses" are a group of surface reactive glass-ceramic biomaterials. They are biocompatible and bioactive, thus being useful as implant materials in the human body to repair and replace diseased or damaged bone.

The term "promoting osteogenesis" has the meaning generally understood in the art; i.e. promoting the development and formation of bone. Osteogenesis is also known as ossification and is the process of laying down new bone material by cells called osteoblasts.

Another aspect of the invention relates to a bone bioactive composition comprising a water-based salt solution comprising sodium dihydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, potassium chloride in a concentration from 2.3 to 3.1 mM in the solution, a calcium salt in a concentration from 7 to 15 mM in the solution, a salt of a divalent metal different from calcium in a concentration from 2 to 12 mM in the solution, and a chelating agent.

Another aspect of the invention is the bone bioactive composition as described above for use in promoting osteogenesis.

Another aspect of the invention is a kit comprising a composition as described above and an implant.

Another aspect of the invention is the use of the kits mentioned above in promoting osteogenesis.

Another aspect of the invention is a process for preparing the composition according to the first aspect comprising mixing all the elements in solid form of the composition with water until complete homogenization.

Another aspect of the invention relates to the use of a bone bioactive composition, according to the first aspect, for treating the surface of a metal implant prior implantation.

It is believed that the present invention provides the first liquid composition that promotes osteogenesis, with a very easy application and particularly useful when a metal implant is used. Therefore, with the composition of the invention it is not needed to modify the implant surface in order to improve protein binding and osteointegration of implants; which are the strategies currently used in the art. Without being limited to theory, it is believed that the compositions herein proposed promote osteogenesis, favoring bone formation, increasing the production of bone tissue and also improving the quality of the bone produced. This is observed in Example 1 provided below, where influence of the bone bioactive composition in the expression of bone markers in in vitro cell cultures is studied. The different expression of genes shown in FIGS. 1 and 2 is correlated with the favoring of bone formation. In addition, when the implant is treated with the bone bioactive composition of the present invention, the production of bone is increased and the quality of the produced bone is higher.

As a second advantageous point, the bone bioactive composition greatly accelerates the process of bone formation. This finding is confirmed with the study in Example 2 and FIG. 3 of the influence of the bone bioactive composition in the calcium excretion and Alcaline Phosphatase (ALP) activity during bone formation in in vitro cell cultures. It can be seen that in the case of cell cultures with implant discs treated with the bone bioactive composition, the peak of calcium excretion can be seen earlier (see increase in day 3), showing an earlier formation of the bone (FIG. 3). Regarding ALP, an increase in the activity of said protein is also related with bone formation. Results obtained for ALP activity appear summarized in FIG. 4. A similar trend as the one seen in FIG. 3 can be seen in FIG. 4, i.e. early peak on day 3 of ALP activity showing early bone formation. Therefore, results obtained for calcium concentration and ALP activity perfectly correlate and are consistent with an early bone formation induced by the bone bioactive composition of the present invention.

These observations are confirmed in vivo when studying the influence of the bone bioactive composition in the implant-bone engraftment in rabbits (Example 3). For this study 60 dental implant were used divided into three groups: A implant without treatment; B implant+bone active composition at pH 7.4; and C implant+bone active composition at pH 7.6. In general terms, from FIGS. 5 to 7 it can be seen that an earlier formation of bone is induced in Groups B and C (even earlier and greater in the latter). This difference was maintained all throughout the experimental time frame (i.e., until day 60). In addition, from table 3 it is also derivable an earlier and increased BIC (Bone-to-Implant Contact) in groups B and C compared to group A. In addition, and surprisingly, as also seen in FIGS. 5 to 7, group C showed also an increase in all time points when compared with group B.

Thus, remarkably, without the compositions and kits of the invention a dental implant takes three months to properly engraft, while using the compositions and kits of the invention, engraftment is greatly accelerated and only takes 15 days. This represents a great advantage for the patient and the doctor.

It has been observed in the experiments herein provided (e.g. Example 4 and FIG. 9) that different compositions described above are useful in promoting osteogenesis. Specifically FIG. 9 shows that basic PBS composition enhances bone growth. Two different commercial PBS were additionally tested and all of them gave similar results. Commercial PBS, which contains low concentrations of $CaCl_2$+$MgCl_2$, also enhances bone growth. Additionally, the combination PBS+EDTA enhances bone growth in a similar extension that PBS. Nevertheless, remarkably, the combination PBS+$CaCl_2$+$MgCl_2$ with higher concentrations of $CaCl_2$+$MgCl_2$ presents more osteogenic capacity in comparison with treatment with only PBS or PBS+EDTA and the combination of PBS+$CaCl_2$+$MgCl_2$+EDTA shows and even more surprising osteogenic capacity compared to the other treatments.

Furthermore, example 6 shows that the bone bioactive composition is able to promote osteogenesis in combination with a great variety of materials, also when using biomaterials for bone reconstruction (like xenografts or ground teeth material) instead of metal implants.

Remarkably, the bone bioactive composition is able to promote osteogenesis without presence of implant. Results of example 7 show, due to the use of the bone bioactive composition, an improved calcification of the cementoblast-like cells together with a recuperation of the collagen fibrils of the periodontal ligament, which is the major defect in periodontitis.

The compositions of the invention also show relevant advantages from a practical point of view. All the elements of the bone bioactive composition are used in GMP condition; the composition can be used to any kind of titanium surface; its manufacture is not convoluted and is not expensive; the procedure is very easy because the implant is submerged only 2 minutes in the bone bioactive composition prior to insertion into bone, thus, the bone bioactive composition handling is effortless in surgical procedures for bone regeneration or peri-implantitis.

The detailed description and examples shown below are presented for the purposes of providing those skilled in the art with a sufficiently clear and complete explanation of this invention, but should not be considered limitations on the essential aspects contemplated therein, as presented in earlier sections of this description.

DETAILED DESCRIPTION OF THE INVENTION

Composition Comprising Water-Based Salt Solution and Preparation Thereof

The invention provides a bone bioactive composition comprising a water-based salt solution comprising sodium dihydrogen phosphate and sodium chloride, which is useful in for use in promoting osteogenesis.

In a particular embodiment, sodium dihydrogen phosphate is in a concentration from 8 to 12 mM in the solution and sodium chloride is in a concentration from 130 to 140 mM in the solution. Particularly, sodium dihydrogen phosphate is in a concentration from 9 to 11 mM in the solution. Preferably, the concentration of sodium dihydrogen phosphate is in a value or in a subrange between the range 8 to 12 mM, that is, at 8 mM, 8.5 mM, 9 mM, 9.5 mM, 10 mM, 10.5 mM, 11 mM, 11.5 mM or 12 mM. More preferably, the concentration of sodium dihydrogen phosphate is 10 mM and more preferably, 10.14 mM.

Independently, in a particular embodiment, sodium chloride is in a concentration from 130 to 140 mM in the solution. Particularly, sodium chloride is in a concentration from 132 to 138 mM in the solution. Preferably, the concentration of sodium chloride is in a value or in a subrange between the range 130 to 140 mM, that is, at 130 mM, 130.5 mM, 131 mM, 131.5 mM, 132 mM, 132.5 mM, 133 mM, 133.5 mM, 134 mM, 134.5 mM, 135 mM, 135.5 mM, 136 mM, 136.5 mM, 137 mM, 137.5 mM, 138 mM, 138.5 mM, 139 mM, 139.5 mM or 140 mM. More preferably, the concentration of sodium chloride is 137 mM, and more exactly, 136.99 mM.

In a particular embodiment, the water-based salt solution further comprises potassium hydrogen phosphate or potassium chloride.

In another particular embodiment, the water-based salt solution further comprises potassium hydrogen phosphate and potassium chloride.

In a more particular embodiment, potassium hydrogen phosphate is in a concentration from 1.4 to 2.2 mM in the solution. Particularly, potassium hydrogen phosphate is in a concentration from 1.6 to 2 mM in the solution. Preferably, the concentration of potassium hydrogen phosphate is in a value or in a subrange between the range 1.4 to 2.2 mM, that is, at 1.4 mM, 1.5 mM, 1.6 mM, 1.7 mM, 1.8 mM, 1.9 mM, 2.0 mM, 2.1 mM or 2.2. mM. More preferably, the concentration of potassium hydrogen phosphate is 1.8 mM and more preferably, 1.76 mM.

In another particular embodiment, potassium chloride is in a concentration from 2.3 to 3.1 mM in the solution. More particularly, potassium chloride is in a concentration from 2.5 to 2.9 mM in the solution. Preferably, the concentration of potassium chloride is in a value or in a subrange between the range 2.3 to 3.1 mM, that is, at 2.3 mM, 2.4 mM, 2.5 mM, 2.6 mM, 2.7 mM, 2.8 mM, 2.9 mM, 3.0 mM, or 3.1 mM. More preferably, the concentration of potassium chloride is 2.7 mM, and more exactly, 2.68 mM.

In a particular embodiment, the pH of the solution is between 7.0 and 8.0. More particularly, the pH is between 7.0 and 7.8. Particularly, the pH is in a value or in a subrange between the range 7.0 and 8.0, that is at 7.0, 7.1, 7.2, 7.3, 7.4, 7.5, 7.6, 7.7, 7.8, 7.9 or 8.0. More preferably, the pH is between 7.4 and 7.8. More preferably, the pH is between 7.5 and 7.7. More preferably, the pH of the solution is 7.6. It is noteworthy, that, surprisingly, the composition of the present invention at pH 7.6 shows even increased effects, as it will be apparent from the examples included below. More specifically, the composition of the present invention, when used at said pH showed an even earlier bone formation and an increased bone formation.

In a particular embodiment, the water-based salt solution further comprises magnesium chloride and calcium chloride. Alternatively, the solution can comprise one salt of magnesium and one salt of calcium with a counterion different but equivalent to chloride, that does not interfere in the solution. In another particular embodiment, the solution comprises a calcium salt and a salt of a divalent metal different from calcium. The divalent metal can be e.g. beryllium, magnesium, strontium, barium, radium, zinc, copper, nickel, manganese (2+), iron (2+), chromium (2+), platinum (2+), or mercury (2+). In a particular embodiment, magnesium chloride or the salt of a divalent metal different from calcium is in a concentration from 2 to 12 mM in the solution and calcium chloride or the calcium salt is in a concentration from 7 to 15 mM in the solution. Preferably, magnesium chloride or the salt of a divalent metal different from calcium is in a concentration from 4 to 10 mM. Preferably, the concentration of magnesium chloride or the salt of a divalent metal different from calcium is in a value or in a subrange between the range 2 to 12 mM, that is, at 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10.0 mM, 10.5 mM, 11.0 mM, 11.5 mM or 12.0 mM. More preferably, the concentration of magnesium chloride or the salt of a divalent metal different from calcium in the solution is 8.4 mM.

Independently, in a particular embodiment, calcium chloride or the calcium salt is in a concentration from 7 to 15 mM in the solution. Particularly, calcium chloride or the calcium salt is in a concentration from 9 to 12 mM in the solution. Preferably, the concentration of calcium chloride or the calcium salt is in a value or in a subrange between the range 7 to 15 mM, that is, at 7.0 mM, 7.5 mM, 8.0 mM, 8.5 mM, 9.0 mM, 9.5 mM, 10.0 mM, 10.5 mM, 11.0 mM, 11.5 mM, 12.0 mM, 12.5 mM, 13.0 mM, 13.5 mM, 14.0 mM, 14.5 mM or 15.0 mM. More preferably, the concentration of calcium chloride or the calcium salt is 10.81 mM.

In a particular embodiment, the water-based salt solution further comprises a chelating agent. In a more particular embodiment, the chelating agent is EDTA. In a particular embodiment, the concentration of EDTA in the composition is from 25 mM to 100 mM. Particularly, EDTA is in a concentration from 40 to 80 mM in the solution. Preferably, the concentration of EDTA is in a value or in a subrange between the range 25 mM to 100 mM, and preferably at 68.44 mM.

In another aspect, the invention provides a bone bioactive composition comprising a water-based salt solution comprising sodium dihydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, potassium chloride in a concentration from 2.3 to 3.1 mM in the solution, a calcium salt in a concentration from 7 to 15 mM in the solution, a salt of a divalent metal different from calcium in a concentration from 2 to 12 mM in the solution, and a chelating agent.

In a particular embodiment, the calcium salt is calcium chloride and the salt of a divalent metal different from calcium is magnesium chloride.

In a particular embodiment, the bone bioactive composition for promoting osteogenesis comprises a water-based salt solution comprising sodium dihydrogen phosphate, sodium chloride, potassium hydrogen phosphate, potassium chloride, magnesium chloride, calcium chloride, and EDTA. In a particular embodiment, the composition comprises a water-based salt solution comprising a water-based salt solution comprising 10 mM sodium dihydrogen phosphate, 137 mM sodium chloride, 1.8 mM potassium hydrogen phosphate, 2.7 mM potassium chloride, 8.4 mM magnesium chloride, 10.8 mM calcium chloride and 68.4 mM EDTA. In a more particular embodiment, the composition comprises a water-based salt solution comprising NaCl 136.99 mM, KCl 2.68 mM, Na$_2$HPO$_4$ 10.14 mM, KH$_2$PO$_4$ 1.76 mM, MgCl$_2$ 8.4 mM, CaCl$_2$ 10.81 mM and EDTA 68.44 mM, at a pH of between 7.0 and 7.8, and more preferably of 7.6.

Thus, a bone bioactive composition particularly useful for the purposes of the invention comprises a water-based salt solution comprising 10 mM sodium dihydrogen phosphate, 137 mM sodium chloride, 1.8 mM potassium hydrogen phosphate, 2.7 mM potassium chloride, 8.4 mM magnesium chloride, 10.8 mM calcium chloride and 68.4 mM EDTA. In a particular embodiment the pH of the solution is 7.6.

Another aspect of the invention is related to a bone bioactive composition as defined above, for use in promoting osteogenesis. The examples provided demonstrate that different compositions are useful in the promotion of osteogenesis for the purposes of the invention. These include particularly, compositions based only on sodium dihydrogen phosphate and sodium chloride; compositions further comprising potassium hydrogen phosphate and/or potassium chloride; compositions further comprising magnesium and calcium chloride, and compositions further comprising EDTA.

Some examples of commercially available solutions are described herein as examples of compositions that can also be used for the purposes of the invention. The water-based salt solution used in the invention is often referred as "Phosphate Buffered Saline" (abbreviated PBS). PBS refers to a buffer solution containing at least one phosphate and which is commonly used to perform molecular biology techniques and in cell culture, to perform washes and/or to prepare reagents. The basic components are sodium dihydrogen phosphate and sodium chloride and, in some formulations, potassium chloride and potassium dihydrogen phosphate. The osmolarity and ion concentrations of the solutions match those of the human body (isotonic). PSB can be stored at room temperature.

There are many different ways to prepare PBS solutions. Some formulations do not contain potassium and magnesium, while other ones contain calcium and/or magnesium. Some examples of PBS are described herein.

TABLE A

The most common composition of PBS (1X)

| Salt | Concentration (mmol/L) | Concentration (g/L) |
|---|---|---|
| NaCl | 137 | 8.0 |
| KCl | 2.7 | 0.2 |
| Na2HPO4 | 10 | 1.42 |
| KH2PO4 | 1.8 | 0.24 |

Method of preparation: Start with 800 mL of distilled water to dissolve all salts. Adjust the pH to 7.4 with HCl. Add distilled water to a total volume of 1 liter. The resultant 1×PBS should have a final concentration of 10 mM PO$_4^{3-}$, 137 mM NaCl, and 2.7 mM KCl.

TABLE B

Cold Spring Harbor Protocol:

| reagent | MW | mass (g) 10X | [M] 10X | mass (g) 1X | [M] 1X | [mM] 1x |
|---|---|---|---|---|---|---|
| Na2HPO4 | 141.95897 | 14.1960 | 0.1000 | 1.41960 | 0.0100 | 10.0 |
| KH2PO4 | 136.08569 | 2.4496 | 0.0180 | 0.24496 | 0.0018 | 1.8 |
| NaCl | 58.44300 | 80.0669 | 1.3700 | 8.00669 | 0.1370 | 137.0 |
| KCl | 74.55150 | 2.0129 | 0.0270 | 0.20129 | 0.0027 | 2.7 | pH = 7.4

The pH of the 10× stock solution of PBS is ~6.8, but when diluted with water to 1×PBS it should change to 7.4. When making buffer solutions, it is good practice to always measure the pH directly using a pH meter. If necessary, pH can be adjusted using hydrochloric acid or sodium hydroxide.

The simplest way to prepare a PBS solution is to use PBS buffer tablets or pouches. They are formulated to give a ready-to-use PBS solution upon dissolution in a specified quantity of distilled water. They are available in the standard volumes: 100, 200, 500 and 1000 mL, and 10, 25, 50 and 100 L.

PBS can be stored at room temperature or in the refrigerator. However, concentrated stock solutions may precipitate when cooled and should be kept at room temperature until precipitate has completely dissolved before use.

TABLE C

Phosphate-buffered saline (PBS) (Cold Spring Harbor)

| Reagent | Amount to add (for 1× solution) | Final concentration (1×) | Amount to add (for 10× stock) | Final concentration (10×) |
|---|---|---|---|---|
| NaCl | 8 g | 137 mM | 80 g | 1.37M |
| KCl | 0.2 g | 2.7 mM | 2 g | 27 mM |
| Na$_2$HPO$_4$ | 1.44 g | 10 mM | 14.4 g | 100 mM |
| KH$_2$PO$_4$ | 0.24 g | 1.8 mM | 2.4 g | 18 mM |
| If necessary, PBS may be supplemented with the following: | | | | |
| CaCl$_2$•2H$_2$O | 0.133 g | 1 mM | 1.33 g | 10 mM |
| MgCl$_2$•6H$_2$O | 0.10 g | 0.5 mM | 1.0 g | 5 mM |

PBS can be made as a 1× solution or as a 10× stock. To prepare 1 L of either 1× or 10×PBS, dissolve the reagents listed above in 800 mL of H$_2$O. Adjust the pH to 7.4 (or 7.2, if required) with HCl, and then add H$_2$O to 1 L. Dispense the solution into aliquots and sterilize them by autoclaving for 20 min at 15 psi (1.05 kg/cm$^2$) on liquid cycle or by filter sterilization. Store PBS at room temperature.

For a 10 liter stock of 10×PBS can be prepared by dissolving:
800 g NaCl,
20 g KCl,
144 g Na$_2$HPO$_4$.2H$_2$O
24 g KH$_2$PO$_4$
8 L of distilled water.

After complete mixing, top up final solution to 10 L. The pH of the 10× stock will be approximately 6.8, but when diluted to 1×PBS it should change to 7.4. When making buffer solutions, it is good practice to always measure the pH directly using a pH meter. If necessary, pH can be adjusted using hydrochloric acid or sodium hydroxide.

On dilution, the resultant 1×PBS should have a final concentration of 137 mM NaCl, 10 mM Phosphate, 2.7 mM KCl, and a pH of 7.4.

pH is adjusted with an acid or a base, for instance with hydrochloric acid or phosphoric acid and sodium hydroxide.

PBS is also referred as PBS 10 mM because the concentration of Na$_2$HPO$_4$ is 10 mM (PBS 1×1 L).

Dulbecco's Phosphate Buffered Saline (DPBS): There is no significant difference between PBS and DPBS, unless DPBS has less phosphate concentration; the concentration of Na$_2$HPO$_4$ is 10 mM in PBS and 8.1 mM in DPBS and the concentration of KH$_2$PO$_4$ is 1.8 mM in PBS and 1.41 mM in DPBS.

Product Forms

The composition according to the invention is usually in liquid form ready to be used; therefore it can be commercially sold as liquid in a suitable container, in single doses (e.g. of 1 ml, 2 ml, 3 ml, 5 ml, 10 ml or higher, or in a higher volume (e.g. 25 ml, 50 ml, 100 ml, 1 liter, 10 liters).

The composition can also adopt suitable forms to make the application easier, for example in the form of gel to be applied in the area to be treated or in the tissues surrounding the implant. Thus, in particular embodiments, the composition is in liquid form, in the form of a gel, a varnish or a spray.

In a particular embodiment, the elements of the composition are in solid form, with all the elements of the composition together in a single container or in different containers (e.g. a vial) or in the form of solid tablet, in both cases, to be reconstituted just before use. To this end, the commercial product can comprise the elements of the composition in a container/containers or in the form of tablet, and a volume of water in a container, perfectly measured to be mixed with the solid elements, thus achieving the final solution concentrations specified in other sections of this description. Additionally, water can be acidified or basified in order to obtained the desired pH when mixing with the elements of the composition.

The skilled person will routinely select the amounts of the elements of the composition to obtain a final composition comprising a water-based salt solution depending on the final volumes of composition.

The term "container" herein is used to denote any recipient, having a closure that is suitable for packaging a unit dosage amount of a solid or liquid composition. It will be understood that equivalent forms of packaging, such as a vial, an ampoule, a disposable syringe, a syringe cartridge or a pre-filled syringe, are encompassed by this embodiment of the invention. The containers should be made of a material to preserve stability of the elements of the composition for preferably storing it at room temperature, but also refrigerated.

An aspect of the invention as said above is a kit comprising a composition as defined above and an implant.

The term "implant" is understood widely as any material or scaffold to restore missing bone, in part or in a whole. Implant is understood as synonymous of prosthesis. Depending on the material, implants used in bone tissue engineering can be classified in implants made of metals and alloys (Titanium, Cobalt-Chromium-Molybdenum alloys) and non-metallic implants made basically of ceramics, which can be inert ceramics (alumina, carbon, zirconia) and bioactive ceramics (bioactive glasses and ceramics, calcium phosphates, and hydroxyapatite). Non-metallic implants can also be made of polymers.

Particularly, the implant is a metal implant. The metal implant or the metal prosthesis can be anyone used in odontology and traumatology. In a particular embodiment, the metal implant is a dental implant. Dental implants are usually made of titanium with very specific and accurate tolerances. The most important Titanium alloys for clinical applications are Ti-6Al-4V, Ti-3Al-2.5V and Ti-6Al-7Nb. Dental implants are also made of monolithic Zirconium-oxide. Particularly, the dental metal implant is a dental titanium implant.

In a particular embodiment, the implant is made of a biomaterial. The available bone tissue replacement biomaterials commonly used include autografts, allografts, xenografts and alloplasts. Allografts are derived from a donor of the same species, which may be a fresh/frozen, freeze-dried bone or demineralized freeze-dried bone. Xenografts are obtained from another species and are widely used in clinical periodontal regenerative applications. Alloplastic materials include ceramics and polymers and are either natural or synthetic. Examples of alloplasts are bioactive glasses, calcium phosphates (hydroxyapatite, tricalcium phosphate and other calcium phosphates—brushite, monetite, calcium polyphosphates/CPP-) and calcium sulphate. Particular examples of commercially available bone grafts for bone reconstructive applications are described in Sheikh Z, et al. "Natural graft tissues and synthetic biomaterials for periodontal and alveolar bone reconstructive applications: a review" Biomater Res. 2017; 21: 9.

In a particular embodiment, the kit comprises the implant and the composition of the invention in separate parts. However, in a particular embodiment, the commercial presentation is the implant submerged into the liquid composition in a container. In a particular embodiment, the kit further comprises means to apply the composition; said means are explained hereinafter.

The proposal of the invention can also be useful to promote bone regeneration of areas that are not in contact with an implant but with presence of bone loss. Examples of the above are in case of periodontal diseases. In some cases, the article of manufacture is only the composition in liquid form or in solid form, because the professional has at his disposal the other elements to prepare the composition and to use and apply the composition to the patient (e.g. water and means for application). Nevertheless, another aspect of the invention is a kit comprising a composition according to the first aspect and means to apply the composition to the area to be treated. Particularly, the means to apply the composition are a syringe, a cotton rod and a textile gauze. In a particular embodiment, the means are to apply the composition to the buccal cavity.

Preferred means to apply the composition in case of peri-implantitis or periodontitis (i.e. that an application to the bone pocket is needed) are a mouthguard, also known as occlusal splints, mouthprotector, mouth piece, gumshield, gumguard, nightguard, bite or mouth splint, or bite plane. This is a removable dental appliance to fit the upper or lower arches of teeth.

In another embodiment, also in order to facilitate the use, the kit further comprises means for adding water into the container with the composition in solid form. The means are preferably a syringe equipped with a disposable perforating needle that is used for drawing water from its container and putting into the container with the composition in solid form.

Another aspect of the invention is the use of the kits described above for use in promoting osteogenesis.

Besides the elements cited in this description conforming the water-based solution, the composition of the invention can comprise additional elements, carriers or excipients, adequate to have a biocompatible composition. These products can adopt the form of a pharmaceutical product, a medicament, a food supplement or an oral care product.

The skilled in the art will use other forms of presentation appropriate to the composition of the invention, normally used in the pharmaceutical and chemical reagents industries.

Applications of the Compositions and the Kits

As discussed above, an aspect of the invention relates to a bone bioactive composition as described above, for use in promoting osteogenesis. This aspect can be alternatively formulated as the use of any of the compositions of the invention for the manufacture of a pharmaceutical product, a medicament, a food supplement or an oral care product for promoting osteogenesis. This aspect may be also alternatively formulated as a method for promoting osteogenesis comprising administering to the subject in need thereof an effective amount of any of the compositions of the invention. Alternatively, it can also be formulated as the use of a bone bioactive composition as described above, in promoting osteogenesis. The same aspect can also be formulated as a method of promoting osteogenesis by using a bone bioactive composition as described above.

Thus, the invention provides a bone bioactive composition for use a medicament.

In a particular embodiment, the bone bioactive composition is used in the promotion of osteogenesis when an implant is used.

In a particular embodiment, the metal implant is a dental titanium implant. The use of the composition or the kits of the present invention favor an early engraftment of the metal implant, inducing the earlier formation of the bone around the implant and, also increasing the quantity as well as the quality of bone formed. In addition, the bone formed is of an increased quality. All the above features contribute to an earlier and stronger engraftment of the implant as well as to a reduced implant loss. Without the compositions and kits of the invention a dental implant takes three months to properly engraft, while using the compositions and kits of the invention, engraftment is greatly accelerated and only takes 15 days. This represents a great advantage for the patient and the doctor.

Hence, the compositions or kits of the present invention are used to improve the engraftment of metal implants (preferably dental titanium implants).

In addition, since the composition of the present invention induces early and/or increased ossification it has also been found useful in the treatment of periodontal diseases such as periodontitis and peri-implantitis, two diseases associated with bacterial infections affecting the connective tissue and the dental bone, leading to the destruction thereof and the loss of implants or teeth, respectively. Said composition, due to its capacity for early and accelerated and increased bone generation is also useful for promoting osteogenesis in the treatment of a periodontal disease, such as peri-implantitis and periodontitis. This may be alternatively formulated as a method for the prevention and/or treatment of a periodontal disease, comprising administering to the subject in need thereof an effective amount of any of the compositions of the invention. Remarkably, the bone bioactive composition is able to promote osteogenesis by itself, without presence of a material as happens in periodontitis.

Another aspect of the invention relates to the use of a bone bioactive composition, for treating the surface of a metal implant prior implantation.

The skilled person will select the appropriate volumes of composition according to the surface and condition to be treated. In a particular embodiment, the composition is applied to the area until the bleeding of said area that means that the stem cells have emerged. In a particular embodiment, some milliliters of composition are applied to the area.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

EXAMPLES

Figure 1:
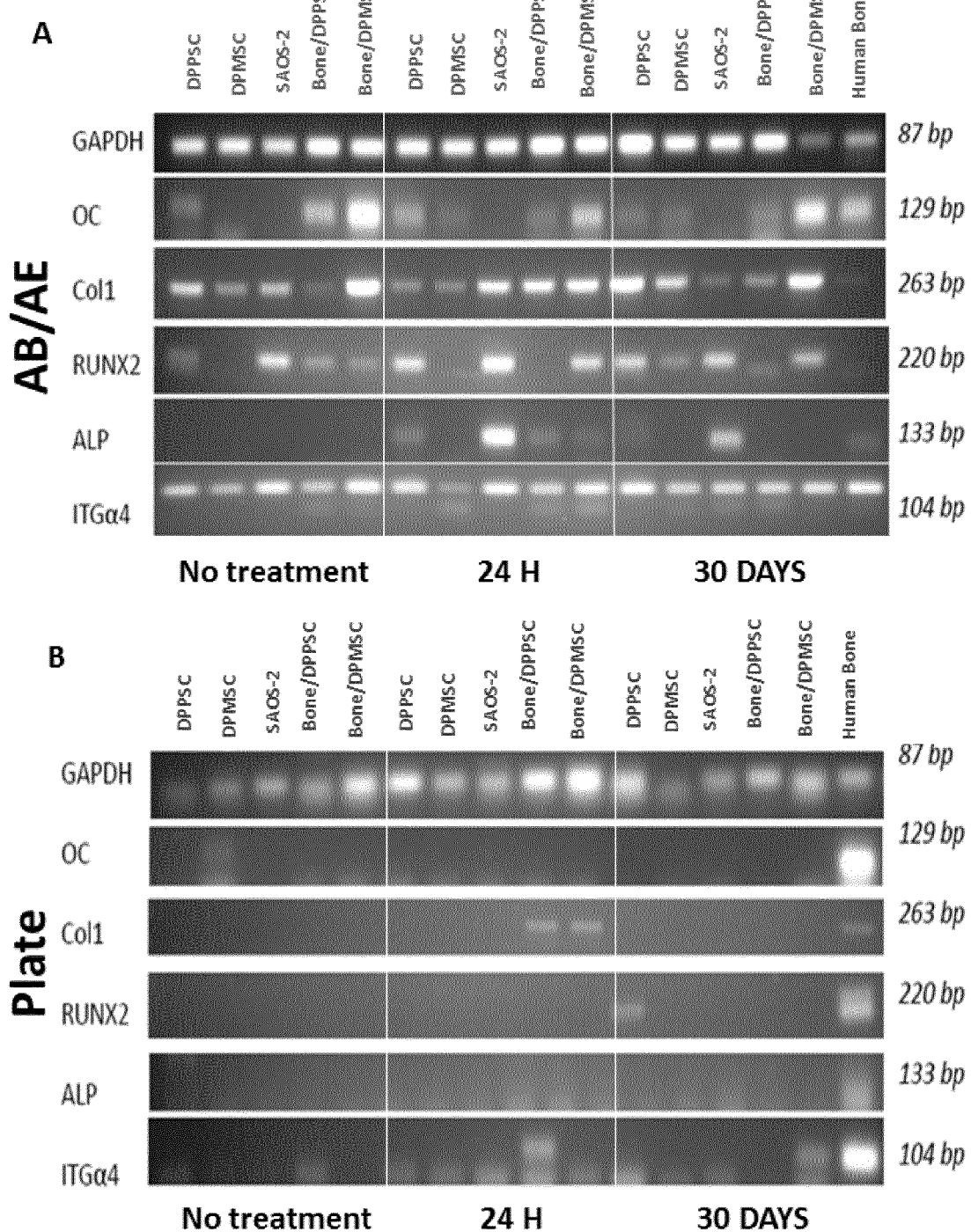
FIG. 1. RT-PCR gene expression analysis of differentiation markers (OC, COL I, RUNX2, ALP and ITGa4) at the second week of cell differentiation. GAPDH was used as a housekeeping gene. A: Titanium disc Ti-6Al-4V (AB/AE) treated with bone bioactive composition. B: Titanium disc Ti-6Al-4V with Calcium phosphate (Plate) treated with bone bioactive composition.

Example 1. Influence of the Bone Bioactive Composition in the Expression of Bone Markers in In Vitro Cell Cultures Cell Isolation:
1. Culture in DPPSC Medium
Cells were cultured on 75 cm² flask with DPPSC medium containing as base medium 60% Dulbecco modified Eagle's medium (DMEM)-low glucose (Sigma, United States) and 40% MCDB-201 (Sigma, United States) supplemented with 1× insulin-transferrin-selenium (hereinafter, ITS; Sigma, United States), 1× linoleic acid-bovine serum albumin (hereinafter, LA-BSA; Sigma, United States), dexamethasone $10^{-9}$M (Sigma, United States), $10^{-4}$ M ascorbic acid 2-phosphate (Sigma, United States), 100 units of penicillin 1000 units of streptomycin (PAA, Life Technologies, USA), 2% foetal bovine serum (hereinafter, FBS; Sigma, United States), 10 ng/ml of Human Platelet Derived Growth Factor-BB (hereinafter, hPDGF-BB; R & D Systems, United States) and 10 ng/ml of Epidermal Growth Factor (hereinafter, EGF; R & D Systems, United States). The flasks were previously covered with 10 ml of 100 ng/ml fibronectin (Life Technologies, USA) and incubated at 37° C., 5% $CO_2$ concentration during 1 hour.

During the two weeks of primary culture, the medium was changed every 3 days and the cells confluence was maintained at 30%, since higher rates of confluence lead to cell maturation and changes in morphology and genotype.

2. Culture in DPMSC Medium (Hereinafter, Cells Cultured Under these Conditions are Referred as DPMSCs)
Cells were cultured on 75 cm² flask with DPMSC medium containing Dulbecco modified Eagle's medium (DMEM) (Biochrom, United Kingdom) supplemented with 2 ng/ml basic Fibroblast Growth Factor (hereinafter, bFGF) and 10% FBS (Hyclone, USA). The flasks were previously covered with 10 ml of 100 ng/ml fibronectin (Life Technologies, USA) and incubated at 37° C., 5% CO2 concentration during 1 hour.

Cells were seeded at 300,000 cells/cm² density, and the medium was changed every three days. The confluence was settled at 50-80% in order to maintain cell morphology and multipotency.

3. Culture in Saos Medium (Hereinafter, Cells Cultured Under these Conditions are Referred as Saos Cells)
Subculture P 12 cells were seeded at 500,000 cells/cm² density, and the medium was changed every three days. The confluence was settled at 80% were unfreezed and seeded in 75 cm² flasks with Saos medium containing DMEM (Invitrogen, United States), supplemented with 10% FBS ([Hyclone, USA]), 2 mm L-Glutamine (Sigma USA), 100 u/ml penicillin (Life Technologies, USA), 1000 u/ml streptomycin (Life Technologies, USA), The flasks were previously covered with 10 ml of 100 ng/mlfibronectin (Life Technologies, USA) and incubated at 37° C., 5% $CO_2$ concentration during 1 hour.

The medium was changed every three days. The subcultures were done when cells were at 80% of confluence.

Preparation of the Implants:
To analyze the influence of the bone bioactive composition of the present invention in the interaction between the above-mentioned cell cultures and metal implants (more precisely, dental titanium implants), discs from the implants were prepared and treated as follows:

Titanium discs were obtained by cutting commercially available titanium alloy $Ti_6Al_4V$ (Ti-6Al-4V), also other discs where obtained from other titanium alloys, in particular Ti-6Al-4V Eli and Ti-5Al-2.5Sn. There were no differences in behavior between discs. The discs measured 2.0 mm in thickness and had a diameter of 14.0 mm. The surface of said discs was then alumina-blasted and acid-etched (hereinafter, AB/AE) which proportioned roughness and increased the implant (disc) surface area. The form of the probes (whether discs, plates or whatever other shape) has no influence on the results.

Preparation of the Bone Bioactive Composition:
8 g of NaCl, 0.2 g of KCl, 1.44 g of $Na_2HPO_4$, 0.24 g of $KH_2PO_4$, 0.80 g of $MgCl_2$, 1.20 g of $CaCl_2$ and 20 g of EDTA were dissolved in 800 ml of water. After all the components were correctly dissolved the volume of the solution was brought to 1 l. Prior to contacting the above-mentioned discs with the cell cultures, the discs were treated with 100 microliters of the bone bioactive composition, incubated at room temperature (37° C. for 1 day). This surface treatment was divided into three groups: surface treatment evaluation at 1 day, 1 month of cell culture and no surface treatment.

Osteoblast Differentiation:
To analyze osteoblast differentiation, the three cell populations mentioned above were cultured, independently, on the titanium discs. Cells were seeded in titanium discs of $Ti_6Al_4V$ discs (treated as mentioned above, i.e., discs treated AB/AE and incubated or not with the bone bioactive composition of the present invention) in 24-well plates at a density of 1×10³ cells per cm². For the different cell types used, the culture conditions for osteoblast differentiation were:

DPPSCs and DPMSCs: Passage five DPPSCs and DPMSCs from the same clone were used for osseous differentiation with osteogenic medium, which contained; as base medium α-MEM (Gibco) and RPMI, supplemented with 10% FBS, 10 mM β-glycerol phosphate (Sigma, United States), 50 mM L-ascorbic acid (Sigma, United States)), dexamethasone 0.01 mM and 1% solution of penicillin/streptomycin. The suspension was tipped out in 75 cm² flasks including the titanium disks with the different treatments mentioned above. The medium was changed every 3 days.

Saos cells were cultured under the same conditions except for the medium, which was the same as mentioned above for these cells.

Bearing in mind the above cell culture conditions, the following groups were generated and analyzed to see if there were differences in the expression of several markers of osteodifferentiation, mainly OC, COL I, RUNX-2, ALP and ITGα4. As housekeeping gene, the expression of GAPFH was also analyzed:

DPPSCs cultured with non-treated (i.e., without the bone bioactive composition) implant disc and under non-differentiating conditions.
DPMSCs cultured with non-treated (i.e., without the bone bioactive composition) implant disk and under non-differentiating conditions.
Saos cells with non-treated (i.e., without the bone bioactive composition) implant disc.
DPPSCs cultured with non-treated (i.e., without the bone bioactive composition) implant disc and under osteoblast differentiating conditions.
DPMSCs cultured with non-treated (i.e., without the bone bioactive composition) implant disk and under osteoblast differentiating conditions.
DPPSCs cultured with treated (i.e., with the bone bioactive composition) implant disc and under non-differentiating conditions during 24 hours.
DPMSCs cultured with treated (i.e., with the bone bioactive composition) implant disk and under non-differentiating conditions during 24 hours.
Saos cells with treated (i.e., with the bone bioactive composition) implant disc during 24 hours.
DPPSCs cultured with treated (i.e., with the bone bioactive composition) implant disk and under osteoblast differentiating conditions during 24 hours.
DPMSCs cultured with treated (i.e., with the bone bioactive composition) implant disk and under osteoblast differentiating conditions during 24 hours.
DPPSCs cultured with treated (i.e., with the bone bioactive composition) implant disc and under non-differentiating conditions during 30 days.
DPMSCs cultured with treated (i.e., with the bone bioactive composition) implant disk and under non-differentiating conditions during 30 days.
Saos cells with treated (i.e., with the bone bioactive composition) implant disc during 30 days.
DPPSCs cultured with treated (i.e., with the bone bioactive composition) implant disk and under osteoblast differentiating conditions during 30 days.
DPMSCs cultured with treated (i.e., with the bone bioactive composition) implant disk and under osteoblast differentiating conditions during 30 days.
Human bone.
Same groups were also analyzed without implant disk i.e. cultivating the cells with Titanium plate discs covered by calcium phosphate (which causes calcification).

To see the RNA expression of the markers mentioned above, total RNA was extracted at 1 and 30 days of differentiation (and for the controls when was RNA extracted) using Trizol (Invitrogen, United States). The sample was treated with DNAse (Promega, United States) and, RNA was isolated following manufacturer's instructions of UltraClean™ Tissue & Cells RNA Isolation Kit (MoBio, United States). Two (2) µg of RNA aliquots were treated with DNase I (Invitrogen, United States) and reverse-transcribed using Transcriptor First Strand cDNA Synthesis Kit (Roche, Switzerland). RT-PCR was performed using the primers on the following Table 1 for the amplification of OC, COL I, RUNX-2, ALP, ITGα4, and GAPDH.

TABLE 1

Primers used for the amplification of OC, COL I, RUNX-2, ALP, ITGα4, and GAPDH

| GENE | Accession Number | FORWARD PRIMER (5-3) | REVERSE PRIMER (5-3) | PRODUCT SIZE (bp) | USE |
|---|---|---|---|---|---|
| ALP | NM_000478 | GGACATGCAGTACGAGCTGA (SEQ ID NO: 1) | GTCAATTCTGCCTCCTTCCA (SEQ ID NO: 2) | 133 | RT-PCR |
| ALP | NM_000478 | CCGTGGCAACTCTATCTTTGG (SEQ ID NO: 3) | GCCATACAGGATGGCAGTGA (SEQ ID NO: 4) | 79 | qRT-PCR |
| COL1 | NM_000088 | ACTGGTGAGACCTGCGTGTA (SEQ ID NO: 5) | CAGTCTGCTGGTCCATGTA (SEQ ID NO: 6) | 263 | RT-PCR |
| COL1 | NM_000088 | CCCTGGAAAGAATGGAGATGAT (SEQ ID NO: 7) | ACTGAAACCTCTGTGTCCCTTCA (SEQ ID NO: 8) | 139 | qRT-PCR |
| OC | NM_199173 | GTGCAGCCTTTGTGTCCA (SEQ ID NO: 9) | GCTCACACCTCCCTCCT (SEQ ID NO: 10) | 129 | RT-PCR |
| OC | NM_199173 | AAGAGACCCAGGCGCTACC T (SEQ ID NO: 11) | ACC TCGTCACAGTCCGGATTG (SEQ ID NO: 12) | 110 | qRT-PCR |
| RUNX2 | NM_001146038 | TTACTGTCATGGCGGGTAAC (SEQ ID NO: 13) | GGTTCCCGAGGTCCATCTA (SEQ ID NO: 14) | 220 | RT-PCR |

TABLE 1-continued

Primers used for the amplification of OC, COL I, RUNX-2, ALP, ITGα4, and GAPDH

| GENE | Accession Number | FORWARD PRIMER (5-3) | REVERSE PRIMER (5-3) | PRODUCT SIZE (bp) | USE |
|---|---|---|---|---|---|
| RUNX2 | NM_001146038 | AGCAAGGTTCAACGATCTGAGAT (SEQ ID NO: 15) | TTTGTGAAGACGGTTATGGTCAA (SEQ ID NO: 16) | 81 | qRT-PCR |
| ITGα4 | NM_002204 | TCCGAGTCAATGTCCACAGA (SEQ ID NO: 17) | GCTGGGCTACCCTATTCCTC (SEQ ID NO: 18) | 88 | RT-PCR qRT-PCR |
| GAPDH | NM_002046 | CTGGTAAAGTGGATATTGTTGCCATTGGAATCATATTGGAACATGTAAACC (SEQ ID NO: 19) | (SEQ ID NO: 20) | 81 | RT-PCR qRT-PCR |
| BMP2 (Bone morphogenetic protein) | | Forward GCG AAA ACG CCT TAA GTC CA (SEQ ID NO: 21) Reverse GTG GAG TTC AGA TGA TCA GC (SEQ ID NO: 22) | | 20 20 | |
| OCN | | Forward GCAGACCTGACATCCAGTAC (SEQ ID NO: 23) Reverse TAATCTGGACTGCTTGTGGC (SEQ ID NO: 24) | | 57.7 57.7 | |

Said RT-PCR amplifications were run in and agarose gel 2%. Results were visualized under UV Light and are shown in FIG. 1.

Figure 2:
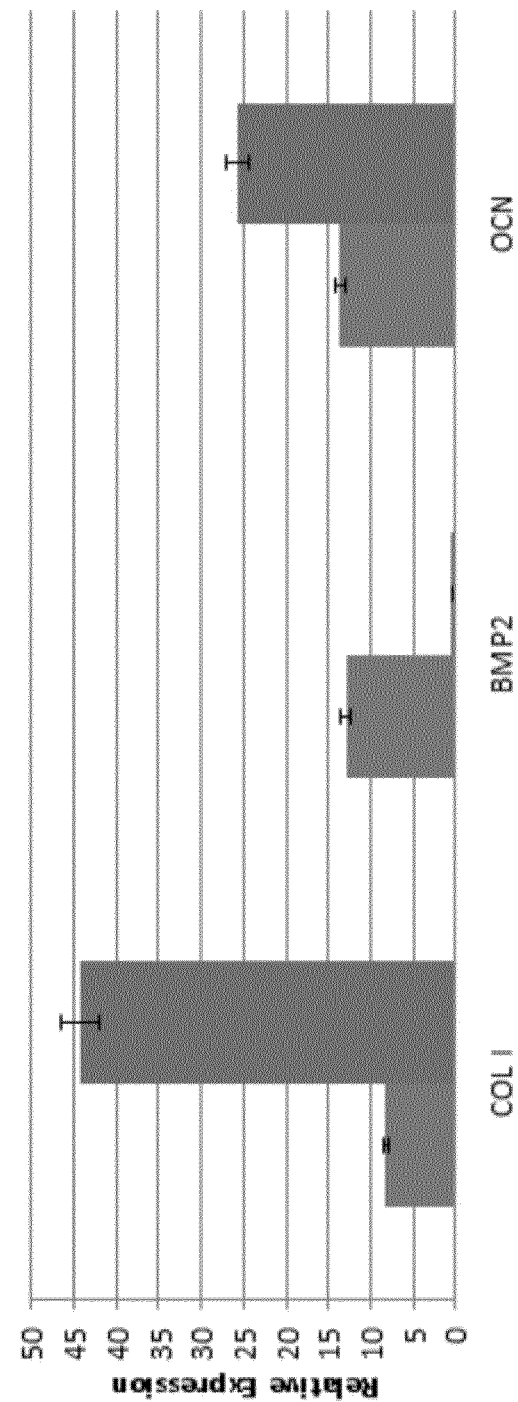
FIG. 2. Q RT-PCR analysis of osteogenic markers (COL I, BMP2 and OCN) of DPPSC at days 21 of cell differentiation. GAPDH was used as a housekeeping gene.

In addition, FIG. 2 shows the results of relative expression for the genes COL I, BMP2 and OCN at day 0 and 30.

Primers used for COL I were the same identified in Table 1.

The different expression of genes shown in FIGS. 1 and 2 is correlated with the favouring of bone formation. In addition, when the implant is treated with the bone bioactive composition of the present invention, the production of bone is increased and the quality of the produced bone is higher.

Example 2. Influence of the Bone Bioactive Composition in the Calcium Excretion and Alcaline Phosphatase (Hereinafter, ALP) Activity During Bone Formation in In Vitro Cell Cultures Calcium concentration in the cell culture medium (i.e., secreted calcium) was measured in DPPSCs and DPMSCs cultured with implant discs treated or not with bone bioactive composition under differentiation conditions, in accordance with what has previously been explained. Said secreted calcium is related with bone formation.

Calcium concentration was measured by analyzing the supernatant of each cell population at days 3, 11 and 20 of differentiation. The analysis was performed using a calcium colorimetric assay kit (BioVision, United States) through a chromogenic complex (λ=575 nm) formed between calcium ions and 0-cresolphthalein. This analysis provides a wavelength detected at 575 nm and this value determines the calcium concentration.

Figure 3:
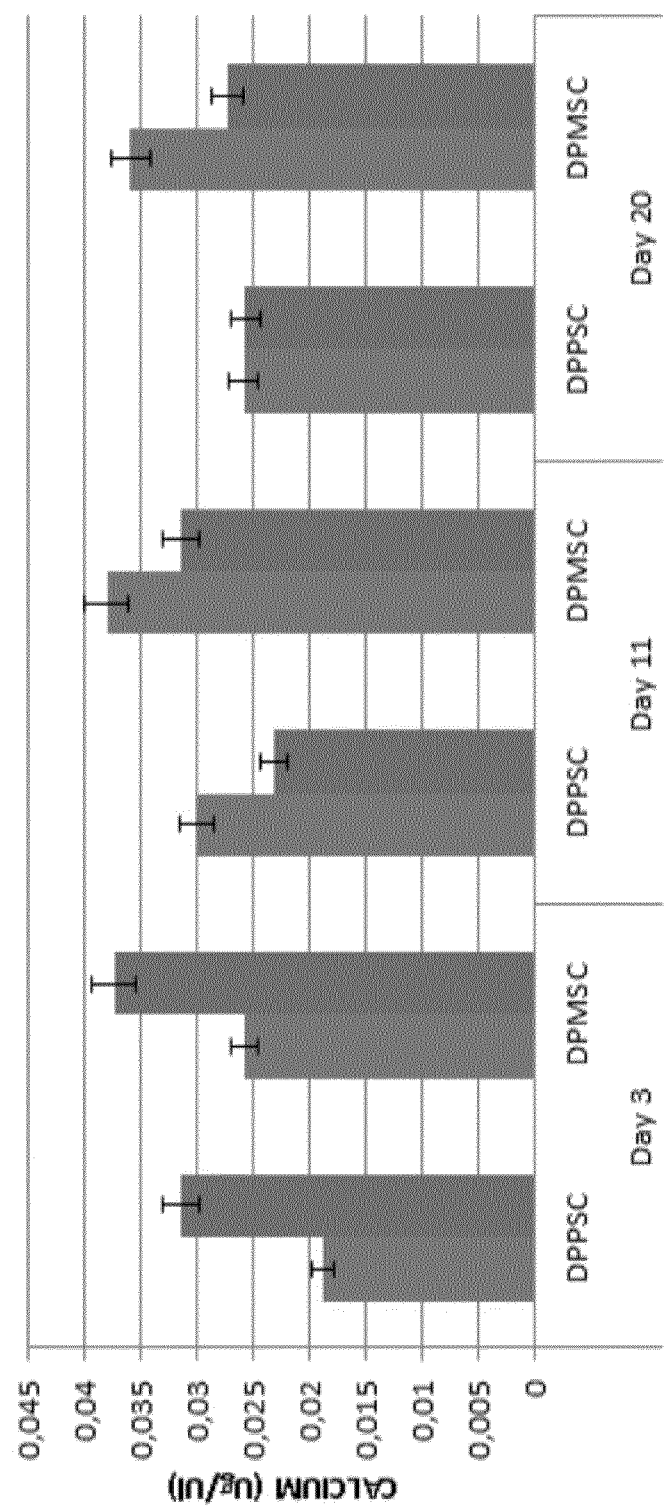
FIG. 3. ALP activity. Calcium activity analysis of DPPSC and DPMSC at days 3, 11 and 20 of cell differentiation on titanium discs treated with bone bioactive composition. GAPDH was used as a housekeeping gene.

Results obtained for calcium concentration are summarized in FIG. 3 It can be see that in the case of cell cultures with implant discs treated with the bone bioactive composition, the peak of calcium excretion can be seen earlier (see increase in day 3), showing an earlier formation of the bone.

Regarding ALP, an increase in the activity of said protein is also related with bone formation. Hence, ALP activity was measured in the supernatant of the above-mentioned cell cultures also at days 3, 11 and 20. Said activity was measured using an alkaline phosphatase kit (BioSystems, USA) according to the manufacturer's instructions. The absorbance of each sample was measured at a wavelength of 405 nm at different times (day 3, 11 and 20 during cell differentiation) wherein an increase in the ALP activity is observed in the treated group vs not treated.

Figure 4:
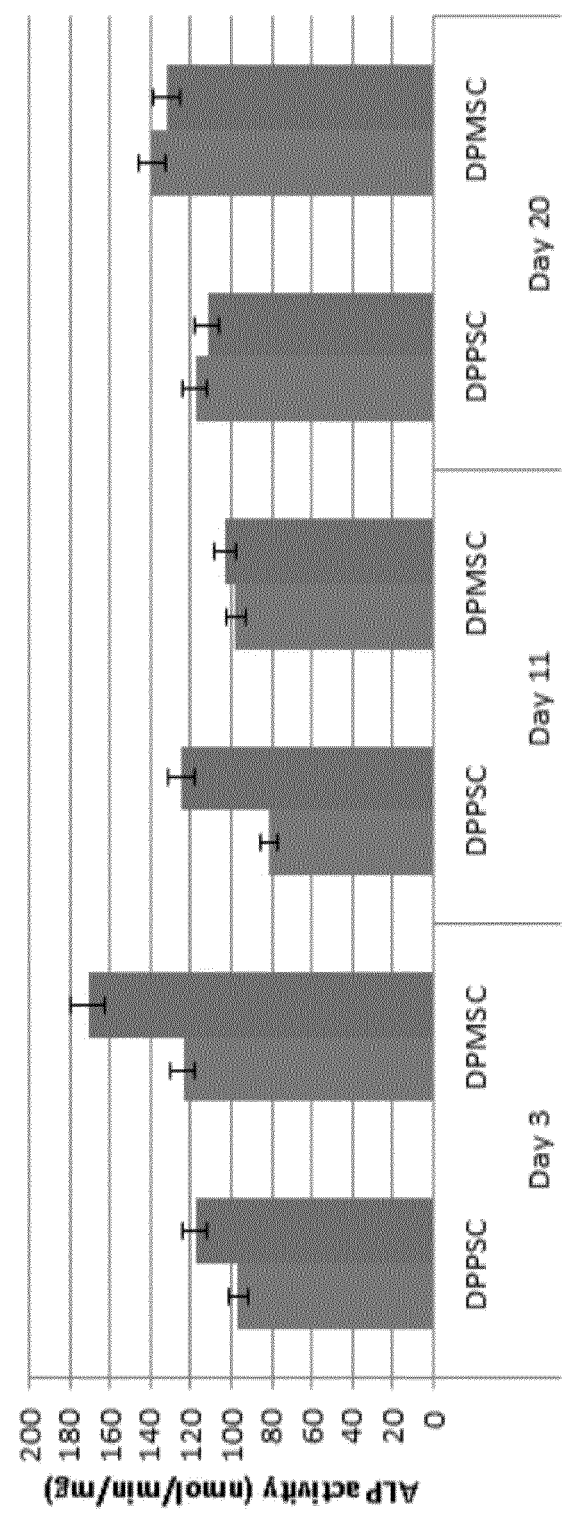
FIG. 4. ALP activity analysis of DPPSC and DPMSC at days 3, 11 and 20 of cell differentiation on titanium discs treated with bone bioactive composition. GAPDH was used as a housekeeping gene.

Results obtained for ALP activity appear summarized in FIG. 4. A similar trend as the one seen in FIG. 3 can be seen in FIG. 4, i.e. early peak on day 3 of ALP activity showing early bone formation.

Therefore, results obtained for calcium concentration and ALP activity perfectly correlate and are consistent with an early bone formation induced by the bone bioactive composition of the present invention.

Example 3. Influence of the Bone Bioactive Composition in the Implant-Bone Engraftment in Rabbits For this study 60 dental implants were used divided into three groups (n=20 per group). Treatment for each of the three study groups appears described in Table 2.

TABLE 2

Details of the additional treatment applied to the implants in the different groups of the study.

| Group | Implant surface treatment |
|---|---|
| A | No additional treatment |
| B | Bone bioactive composition of Example 1, pH adjusted at 7.4 |
| C | Bone bioactive composition of Example 1, pH adjusted at 7.6 |

The implants were treated by blasting with 50-100 μm $TiO_2$ particles, followed by ultrasonic cleaning with an alkaline solution Riozyme IV-E Neutro Gold (Indústria Farmacêutica Rioquímica Ltda, São José do Rio Preto, Brazil), washing with distilled water and pickling with maleic acid ($HO_2CCH_2CHOHCO_2H$). For the implants used in group A the above was the only treatment applied. For experimental groups B and C: the implants were treated initially using the above procedure and after with the corresponding bone bioactive composition using 100 μL for 1 h.

Fifteen adult New Zealand rabbits (*Oryctolagus cuniculus*) with approximately 4.5±0.5 kg were used in this study. Four implants were installed per animal (2 per tibia). The animals were sacrificed 15, 30, 45 and 60 days after surgery.

For the histomosphometric analysis, bone blocks of the tibiae, with inserted implants, were removed from each animal, fixed in 10% of formaldehyde solution for 7 days, and dehydrated in increasing ethanol solutions (60%, 70%, 80%, and 99%) for 24-56 h, as previously described (Yang J et al. "Effects of oestrogen deficiency on rat mandibular and tibial microarchitecture" Dentomaxillofac Radiol 2003 July, 32(4):247-51). Subsequently, the samples were embedded in Technovit 7200 VLC resin (Kultzer & Co., Wehrhein, Germany) and, after curing, samples were sectioned using a metallographical cutter (Isomet 1000; Buehler, Germany). The disc samples were polished using an abrasive paper sequence (Metasery 3000; Buehler, Germany) to a ~30-μm thickness and analyzed using light microscopy (Nikon E200, Japan). The bone growth was measured with respect to the implant platform at the bone contact with the healing abutment, according to the scheme using Image Tool software, version 5.02 for Microsoft Windows™. Two different investigators made the measurements at different times and a unique average of these values was computed. When the measured values were very different both investigators repeated measures.

Figure 5:
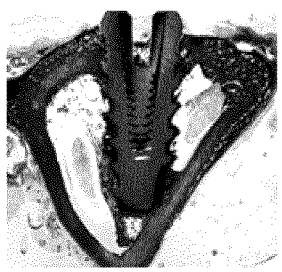
FIG. 5. Histomorphometric analysis of experimental rabbits with group A at 15, 30, 45 and 60 days.
Figure 5:
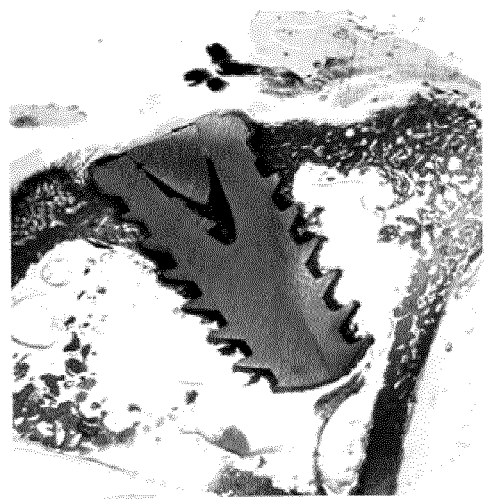
Figure 5:
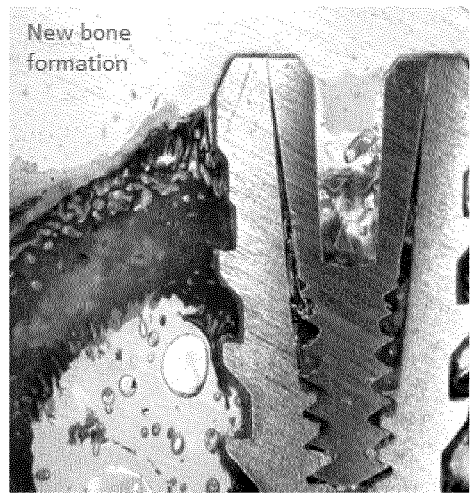
Figure 5:
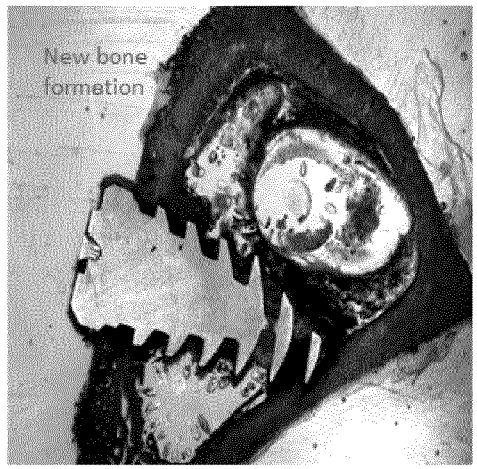
Figure 5:
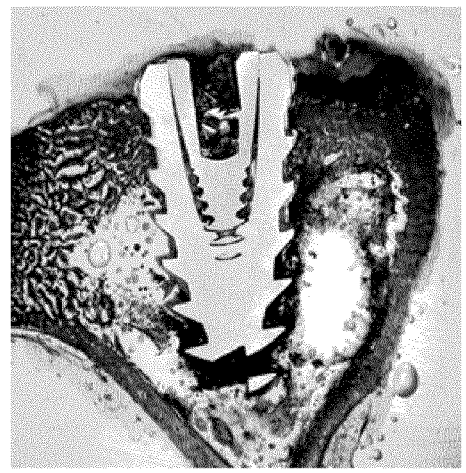
Figure 6:
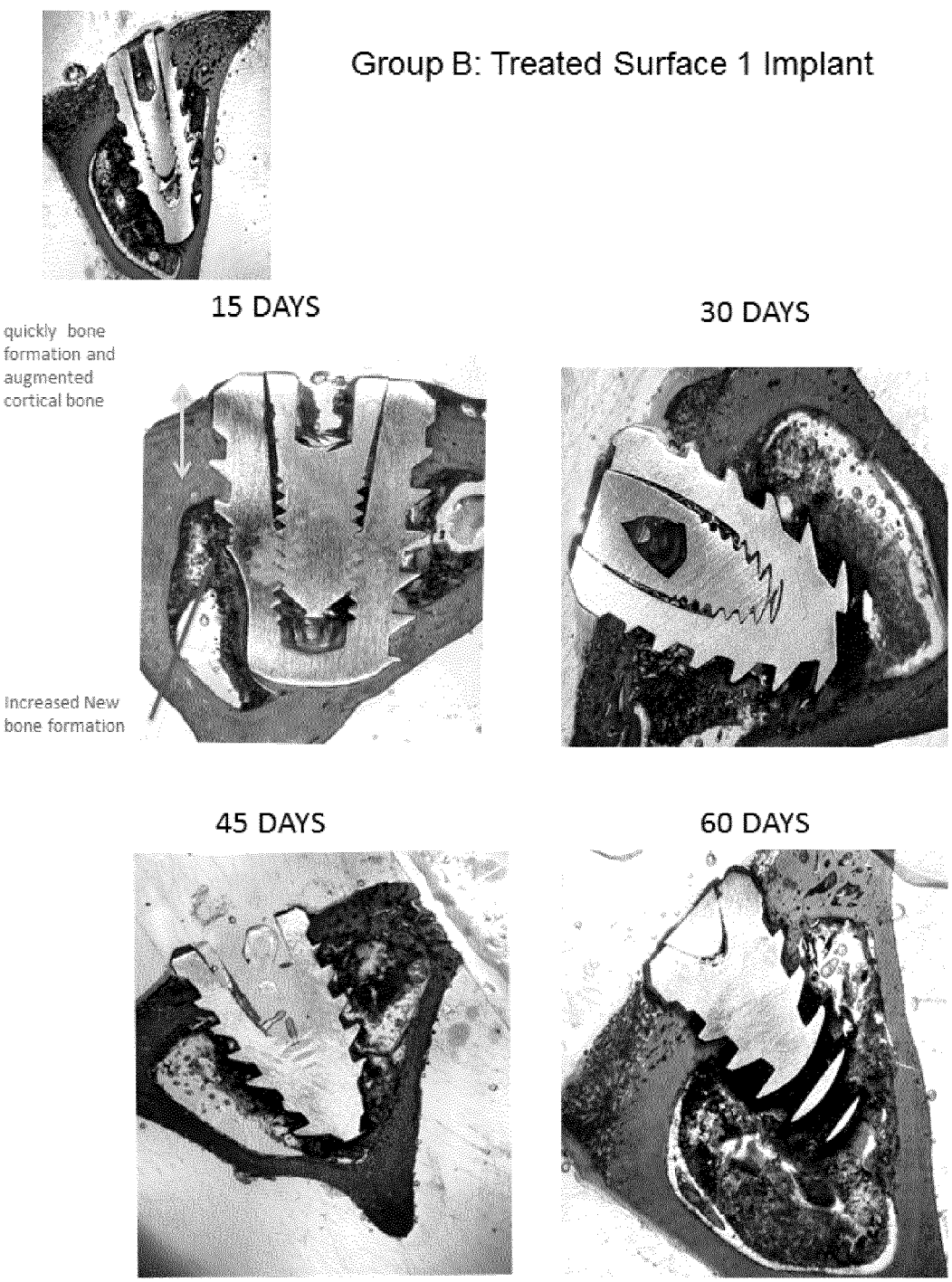
FIG. 6. Histomorphometric analysis of experimental rabbits with group B at 15, 30, 45 and 60 days.
Figure 7:
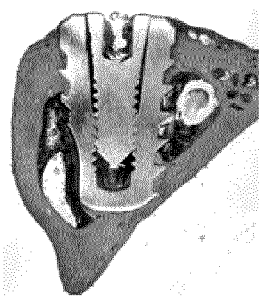
FIG. 7. Histomorphometric analysis of experimental rabbits with group C at 15, 30, 45 and 60 days.
Figure 7:
Figure 7:
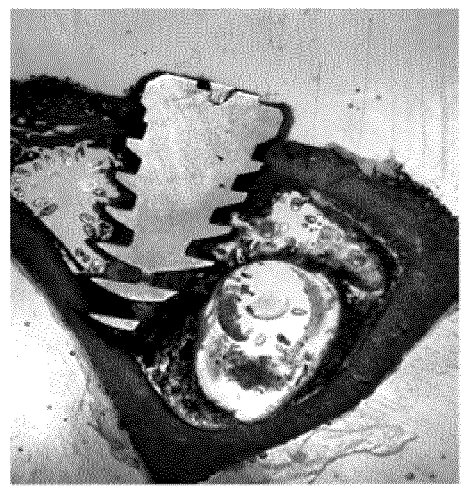
Figure 7:
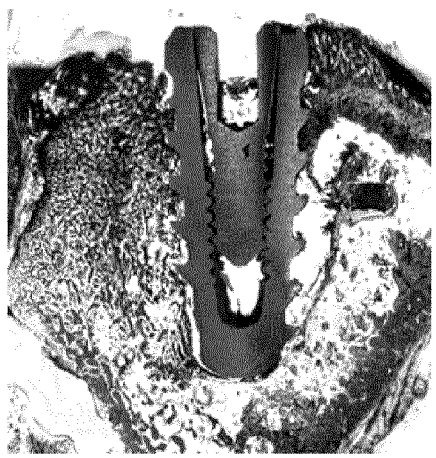
Figure 7:

Obtained results are shown in FIGS. 5, 6 and 7 corresponding to groups A, B and C respectively.

In addition, histological analysis of the samples to measure the Bone-to-Implant Contact (hereinafter, BIC) was performed. Results are summarized in Table 3.

TABLE 3

Results of BIC for the three groups of the study at 15, 30, 45 and 60 days.

| Time of measurement | GROUP A BIC in % (mean ± SD) | GROUP B BIC in % (mean ± SD) | GROUP C BIC in % (mean ± SD) |
| --- | --- | --- | --- |
| 15 Days | 53.8 ± 2.3 | 61.7 ± 1.1 | 68.92 ± 0.3 |
| 30 Days | 56.24 ± 1.8 | 67.4 ± 1.8 | 69.35 ± 2.2 |
| 45 Days | 60.45 ± 1.2 | 68.1 ± 1.6 | 70.34 ± 1.1 |
| 60 Days | 68.29 ± 0.8 | 71.39 ± 1.1 | 73.89 ± 1.9 |

As can be seen in FIGS. 5 to 7, the implants were in contact with predominantly cortical bone along the upper threads in the cortical region, while the threads in the bone marrow were in contact with either newly formed bone or with normal bone marrow. A demarcation line was consistently seen between the newly formed bone and the old bone tissue. In general terms, from said figures it can be seen that an earlier formation of bone is induced in Groups B and C (even earlier and greater in the latter). This difference was maintained all throughout the experimental time frame (i.e., until day 60).

In addition, from table 3 it is also derivable an earlier and increased BIC in groups B and C compared to group A. In addition, and surprisingly, as also seen in FIGS. 5 to 7, group C showed also an increase in all time points when compared with group B.

Finally, the quantity of new bone formed was measured also at 15, 30, 45 and 60 days.

Figure 8:
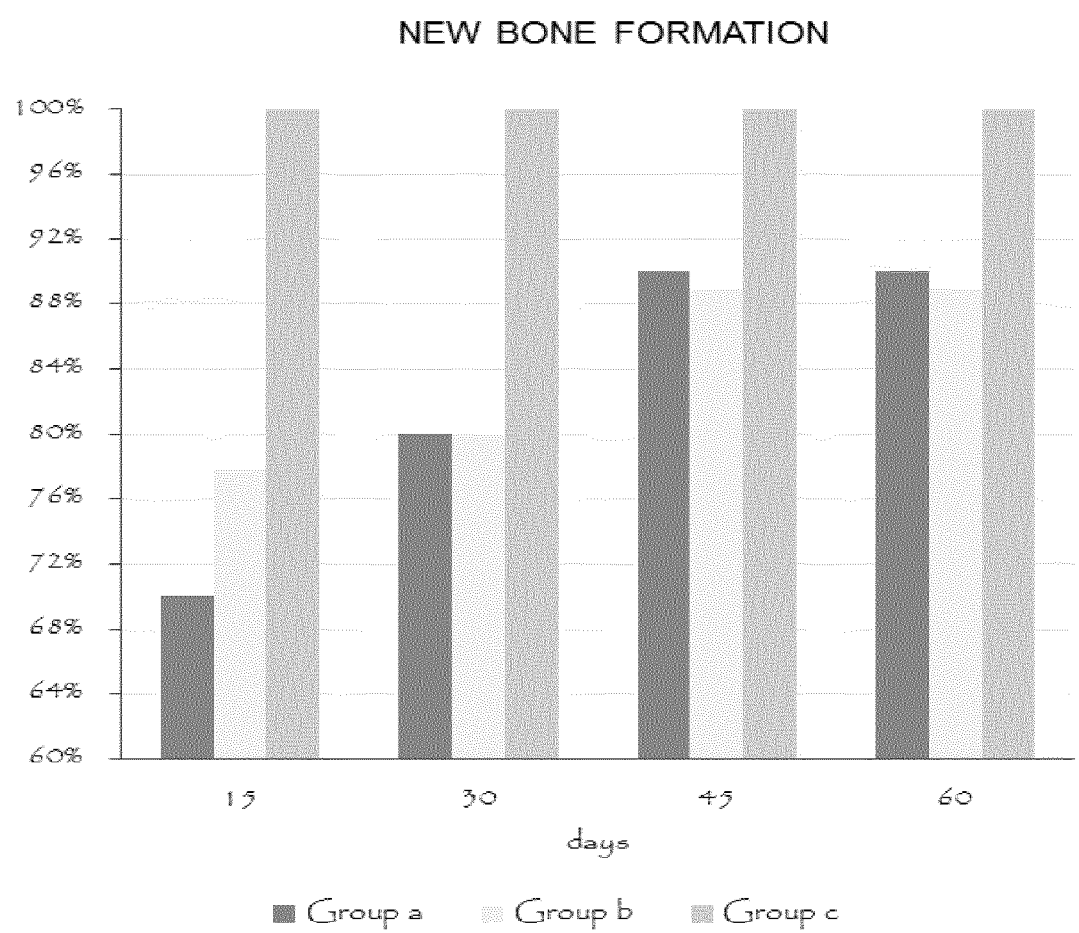
FIG. 8. Quantifications of new bone formation of experimental rabbits with group A, B and C at 15, 30, 45 and 60 days.

Results are summarized in FIG. 8 and are consistent with what has been discussed above. It can be seen an earlier formation of bone in groups B and C (group C shows an even higher bone formation in day 15 when compared with group B). In addition, group C is the only group that surprisingly showed an increase in new bone formed on day 60 (on said day, the quantity of bone formed in groups A and B had evolved to be similar).

Example 4. Comparison Between Treatments 8 g of NaCl, 0.2 g of KCl, 1.44 g of $Na_2HPO_4$, 0.24 g of $KH_2PO_4$, 0.80 g of $MgCl_2$, 1.20 g of $CaCl_2$ and 20 g of EDTA were dissolved in 800 ml of water.

To analyze relative osteogenic capacity of PBS, $CaCl_2$, $MgCl_2$ and EDTA, DPPSC ($1\times10^3$ cells per $cm^2$) were seeded in titanium discs of $Ti_6Al_4V$.

Group 1: treated with PBS (8 g of NaCl, 0.2 g of KCl, 1.44 g of $Na_2HPO_4$, 0.24 g of $KH_2PO_4$, dissolved in 800 ml of water).

Group 2: treated with PBS+$CaCl_2$+$MgCl_2$ (8 g of NaCl, 0.2 g of KCl, 1.44 g of $Na_2HPO_4$, 0.24 g of $KH_2PO_4$, 0.80 g of $MgCl_2$, 1.20 g of $CaCl_2$ dissolved in 800 ml of water).

Group 3: treated with PBS+$CaCl_2$+$MgCl_2$+EDTA (8 g of NaCl, 0.2 g of KCl, 1.44 g of $Na_2HPO_4$, 0.24 g of $KH_2PO_4$, 0.80 g of $MgCl_2$, 1.20 g of $CaCl_2$ and 20 g of EDTA were dissolved in 800 ml of water):

Group 4: treated with PBS+EDTA (8 g of NaCl, 0.2 g of KCl, 1.44 g of $Na_2HPO_4$, 0.24 g of $KH_2PO_4$ and 20 g of EDTA were dissolved in 800 ml of water).

Control: No treated discs.

Discs were treated and incubated during one hour before seeding cells in 24-well plates at a density of $1\times10^3$ cells per $cm^2$. RT-PCR was performed at day 7 of osteoblast differentiation using OC, OCN and ALP. The differences in expression shown in FIG. 9 show that titanium discs treated with PBS with the addition of $CaCl_2$ and $MgCl_2$ presents more osteogenic capacity in comparison with treatment with only PBS or PBS+EDTA and that the combination of PBS, $CaCl_2$, $MgCl_2$ and EDTA shows and even more surprising osteogenic capacity compared to the other treatments.

Figure 9:
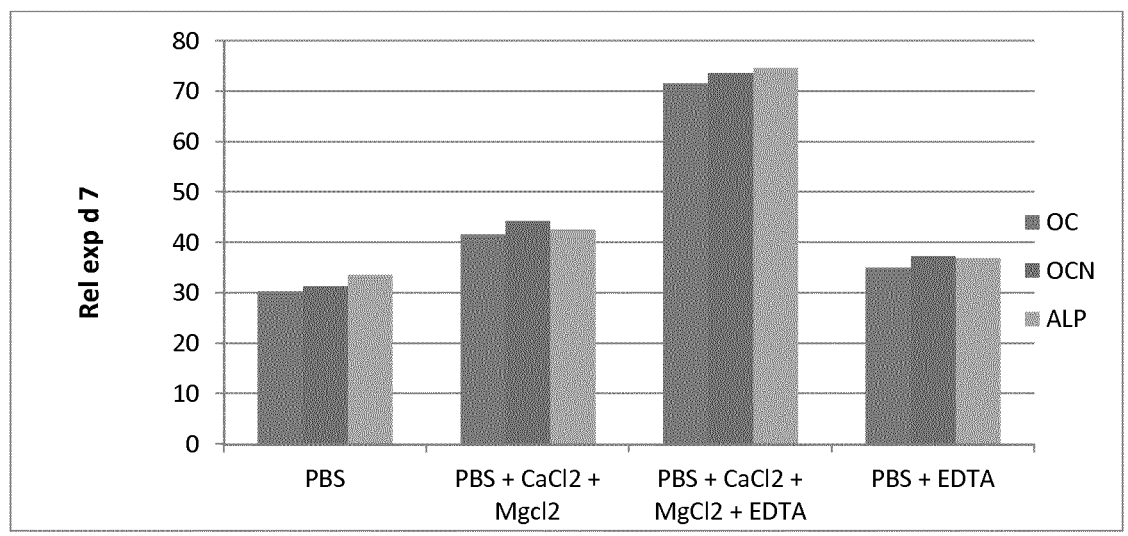
FIG. 9. Q RT-PCR analysis of osteogenic markers (OC, OCN and ALP) of DPPSC at day 7 of cell differentiation on treated titanium discs. GAPDH was used as a housekeeping gene. Expression related to no treatment discs.

Values of FIG. 9 are expressed as expression related to no treated discs at day 7.

Two commercial PBS were also tested and the results were similar to those of the PBS used in the above-mentioned Group 1. Said commercial PBS were: Sigma Aldrich P3813 SIGMA—Phosphate buffered saline (Contents of one pouch, when dissolved in one liter of distilled or deionized water, will yield 0.01 M phosphate buffered saline (NaCl 0.138 M; KCl—0.0027 M); pH 7.4, at 25° C.).

Thermo Fisher CatNum 18912—PBS Tablets. (Phosphate (as sodium phosphates) 10.0 mM, Potassium Chloride (KCl), 2.68 mM, Sodium Chloride (NaCl) 140.0 mM, to be dissolved with 500 ml distilled water).

Example 5. Application of the Composition

Application of the composition in a patient when using an implant: For implants placement using the bone bioactive composition, the drilling sequence bone has to according to the manufacturer's recommendations subsequently implant placing and with very low insertion between 20 to 50 Newtons. This is applicable for dental implants as well as for traumatology implants.

Application of the composition in a patient with periodontitis or peri-implantitis: For the periodontitis treatment using the bone bioactive composition, first of all the conventional periodontal treatment should be done; removing bacterial plaque and granulation tissue by supragingival and subgingival scrapings. In the same intervention, the area of the bone defect has to be well dry before applying the bone bioactive composition using a conventional brush; after that, bleeding is caused until the clot is formed. This process should be done more than once until recuperate all lost bone.

Example 6. In Vivo Study of the Influence of the Bioactive Bone Composition in the Use of Biomaterials in Dog Materials and Methods.

Animals

For this study 3 years old female dog with a weight of 12 kg was used. A specialist for veterinary surgery observed the animal. The Ethics Committee for Animal Research of the University of Murcia approved the protocol of study that followed the guidelines established by the Directive of the Council of the European Union of February, 1st 2013/53/ CEE.

Study Design

The study was designed as an in vivo trial. Dental extraction of all posterior upper and lower molars was performed three months before the study with bone bioactive composition and biomaterials. After that, 12 bone defects were made using a 5 mm trephine, 3 in each zone:
3 defects to test Straumann® XenoGraft alone,
3 for bone bioactive composition with Straumann® XenoGraft,
3 defects for Dentum and
3 for Dentum with bone bioactive composition.

Straumann® XenoGraft is a bovine bone and slow resorption rate similar to human bone with low crystallinity, high porosity and an optimal balance of calcium and phosphate designed to achieve reliable bone volume in guided bone regeneration.

Dentum is used in this description to name a biomaterial formed by autologous dentin. Autologous dentin is used in the clinical procedures as an autograft for its composition almost identical to that of human bone in calcium and phosphorus ions organized as hydroxyapatite and TCP. Dentum was obtained using the Smart Dentin Grinder (distributed by Bioner, Spain, from KometaBio, USA). The teeth extracted from the dog, after being cleaned and dried, were immediately ground using the Smart Dentin Grinder. The tooth particles that were obtained were 300-1200 µm, which were subsequently sieved through a special two-compartment classification system. The particles of teeth were immersed in a basic alcohol cleaner in a sterile vessel to dissolve all organic waste and bacteria during 15 minutes. The particles were then washed with sterile saline solution for 5 minutes and dried.

Figure 10:
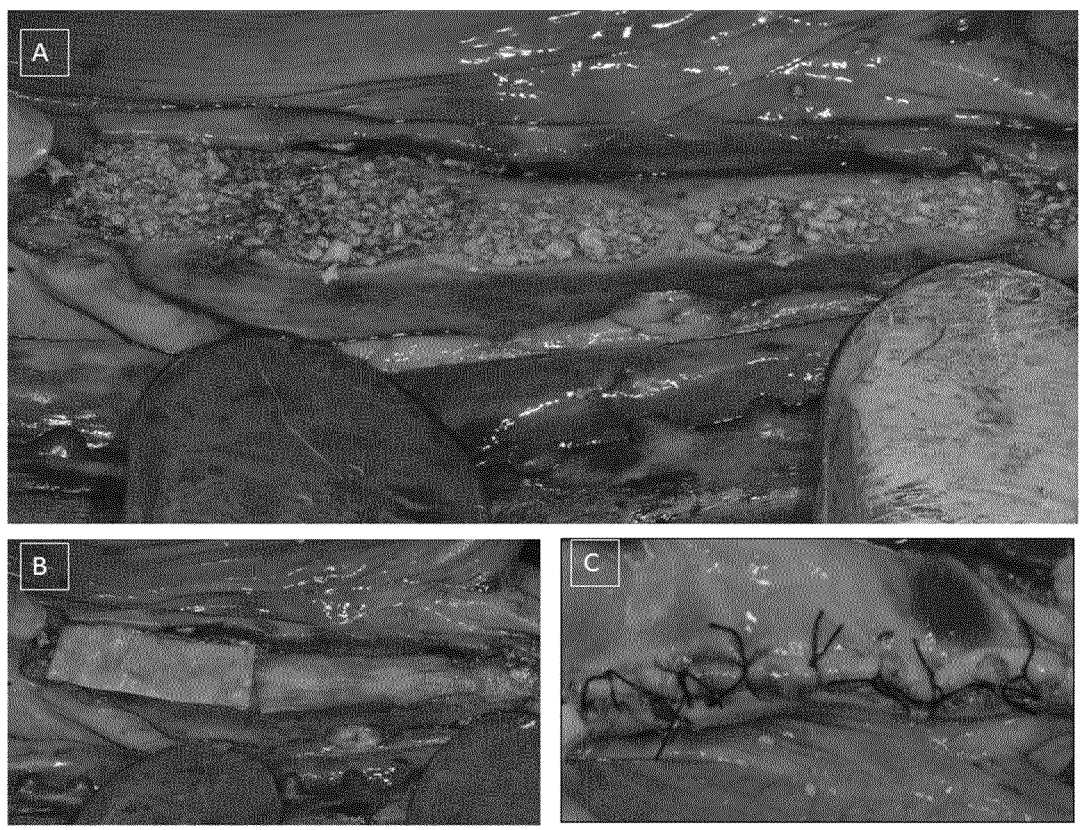
FIG. 10. Surgical procedure for the in vivo study in dog. A. Filling of the 3 bone defects with biomaterial (Straumann® XenoGraft) and the bone bioactive composition. B: Surgical area with membrane. C. Surgical area with 3/0 suture. This figure is related to Example 6.

RX and hilling control of surgical zones was done after 15 days and 2 month of surgery (FIG. 10).

Surgical Procedure

The dog received a pre-anesthetic medication consisting of 0.01 mg/kg atropine (Atropuinsulfat, Braun, B. Braun Melsungen, Melsungen, Germany), 20 mg/kg ketamine hydrochloride (Ketamin 10%, Essex, Munich, Germany), and 0.1 mg/kg xylazine (Rompun, Bayer Vital, Leverkusen, Germany) intramuscularly, followed by an intravenously 2 to 4 mg/kg propofol (Propofol 1% MOT Fresenius, Fresenius Kabi, Bad Homburg, Germany) to induce anesthesia. The maintenance of anesthesia after tracheal intubation was performed by the application of isoflurane with an end-tidal concentration of 1.8% in oxygen/air and a bolus of 0.002 mg/kg/hour fentanyl citrate (Fentanyl-Janssen, Janssen-Cilag, Neuss, Germany) followed by continuous infusion of 0.001 mg/kg/hour fentanyl citrate. To reduce the postoperative pain, analgesia was induced by applying subcutaneous carprofen (Rimadyl, Pfizer, Karlsruhe, Germany) 4 mg/kg every 24 hours for 4 days, starting with the first dose after induction of anesthesia. To sacrifice the animals, an intravenous injection of 50 mg/kg thiopental (Trapanal, Nycomed, Konstanz, Germany) and 2 mmol/kg 7.45% potassium chloride (B. Braun, Melsungen, Germany) was applied.

Histological Evaluation

After sacrifice, samples were obtained and fixed in a 4% formaldehyde solution (Merck, Darmstadt, Germany) for 5-7 days. Following that, samples were dehydrated in an ethanol series of 70%, 80%, 90%, and 100%, remaining 24 hours in each ethanol concentration and defatted in Xylene for 24 hours (Merck, Darmstadt, Germany). For slicing the samples, they were infiltrated embedded and polymerized in Technovit 9100 (Heraeus Kulzer, Wehrheim, Germany) following the instructions manual. The obtained slices were cut to 500 µm by a low-speed rotary diamond saw (Microslice, Metals Research, Cambridge, UK). The sections were placed on opaque acrylic slides (Maertin, Freiburg, Germany) and thickness was reduced to final 60 µm by a rotating grinding plate (Stuers, Ballerup, Denmark). For histological and histometric analysis, incandescent and polarized light microscopy and PC based image analysis were used for the evaluation of bone density.

Figure 11:
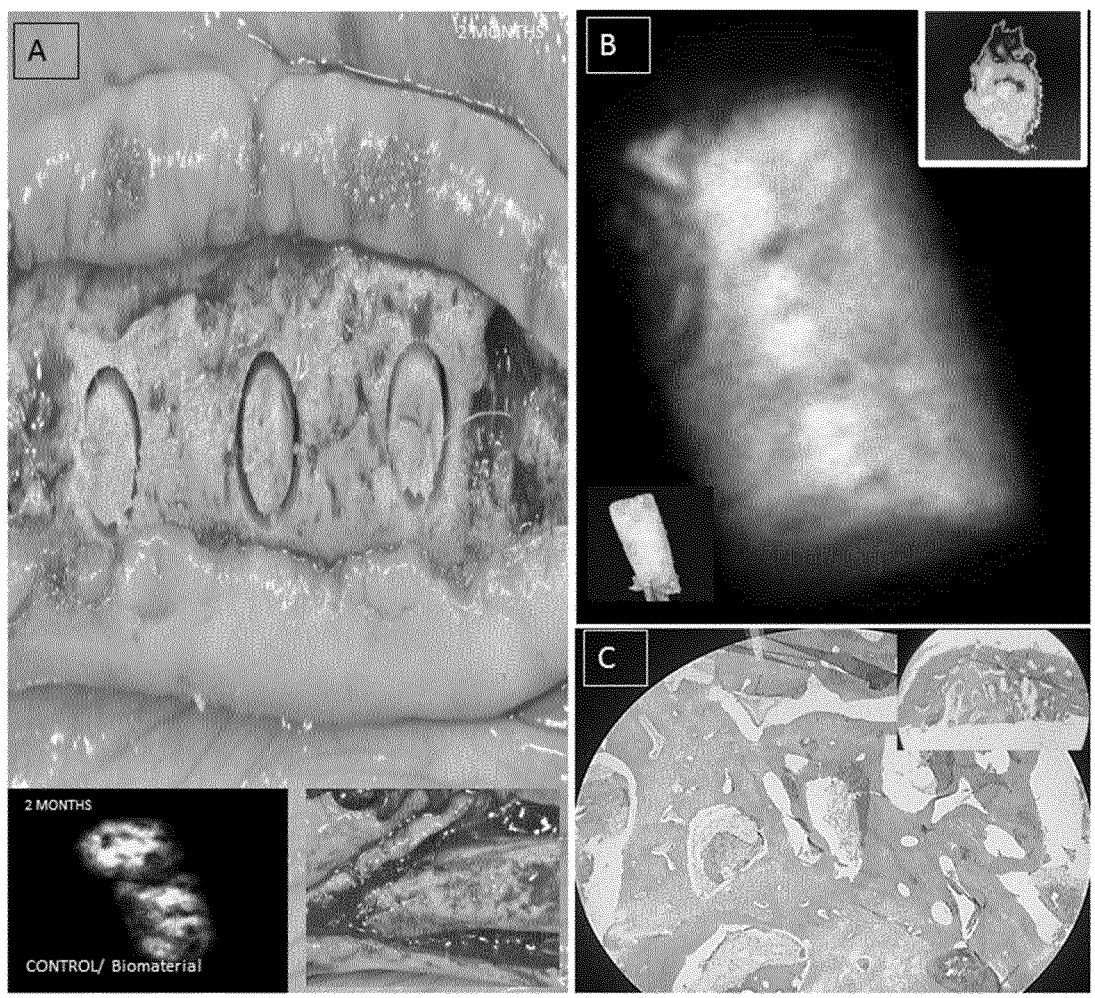
FIG. 11. Evolution of the in vivo study in dog with Straumann® XenoGraft with the bone bioactive composition, 60 days after surgery. A: Sampling after 60 days using a 5 mm trephine (the lower left image corresponds to 2-month with only Straumann® XenoGraft). B: RX analysis. C: Histological analysis. This figure is related to Example 6.

Results:

Homogeneity was detected of the bone tissue and the biomaterial with the bone bioactive composition compared to the control area without bone bioactive composition. The cortical bone consisting of primary and secondary osteons were completely formed. In addition the treated groups had more mature osteoblast and osteocytes when compared to the controls (FIG. 11).

Figure 12:
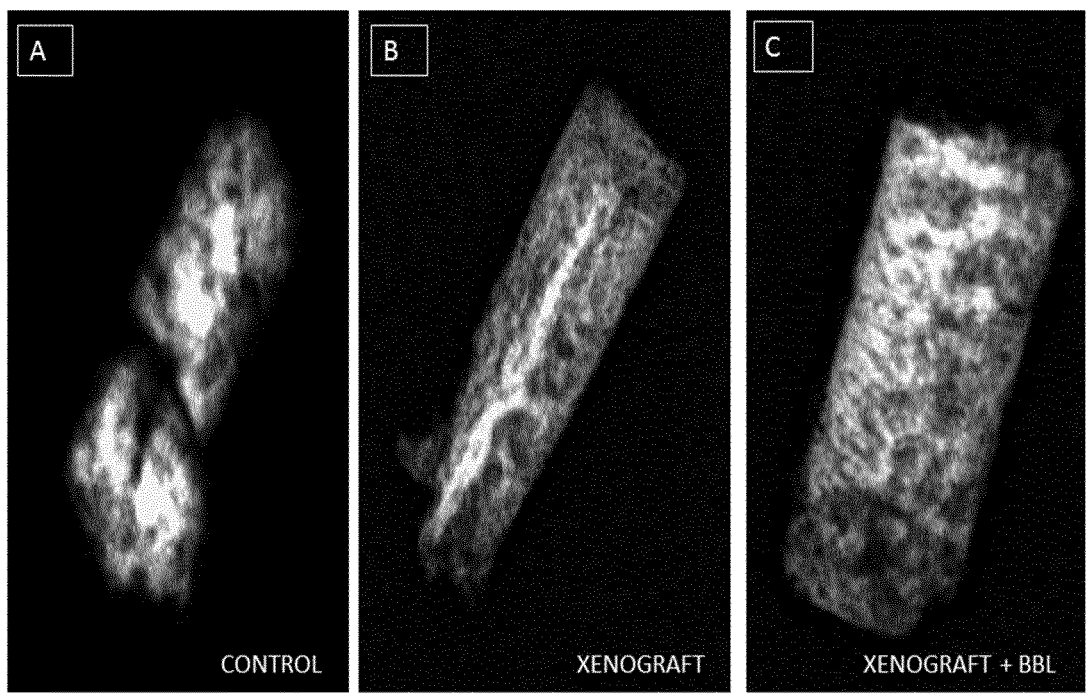
FIG. 12. Sample radiological examination. Comparison between control (no biomaterial), Straumann® XenoGraft alone and Straumann® XenoGraft with Bone bioactive composition (BBL), after 2 months of surgery. This figure is related to Example 5.
Figure 13:
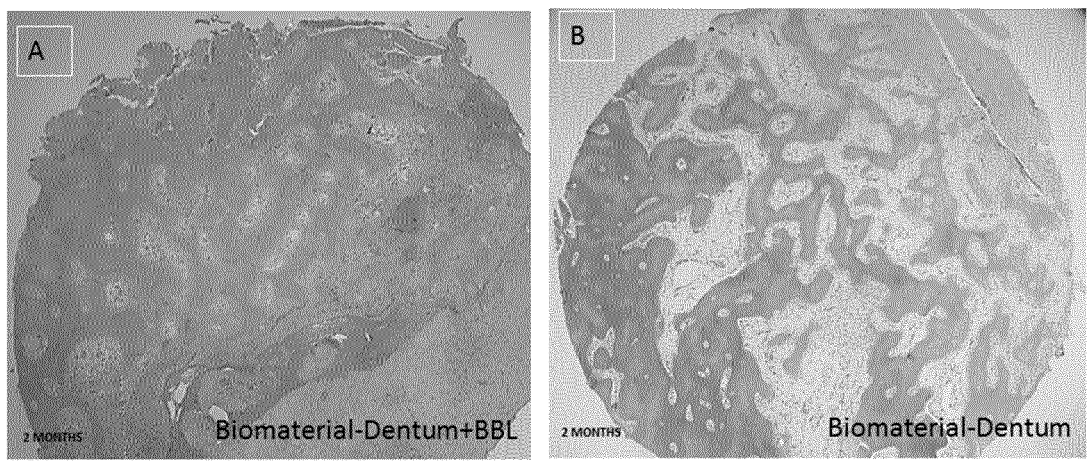
FIG. 13. Histological study. A. Test group: Dentum with bone bioactive composition (BBL). B. Control group: Dentum alone. This figure is related to Example 6.

In the newly formed bone tissue, osteocytes within the lacunae could be detected. New bone was formed integrating the biomaterial and the original bone into the defect zone with a tight connection. (FIGS. 11, 12 and 13). FIG. 13 shows that in (A) the bone defect has regenerated in 80% in the test group (Dentum+bone bioactive composition (BBL)) due to the growth of bone tissue in detriment of the growth of connective tissue—fibroblasts. In (B) with only Dentum, the regeneration of the defect is in a 40% and an extensive presence of connective tissue—not desirable—can be observed.

Example 7. In Vivo Study of the Influence of the Bioactive Bone Composition in Periodontitis Processing of Tooth Samples Human teeth (n=13) were cleaned and the crowns were eliminated.

Transversal sections were obtained after slicing the roots. The teeth blocks were cleaned using a previously described protocol (Galler K M, et al. "Bioengineering of dental stem cells in a PEGylated fibrin gel" Regen Med. 2011, 6(2):191-200). The roots were then washed 3 times in sterile PBS, and then soaked again in 0.5 M EDTA for 10 min, followed by 3 more rinses in BBL. Afterwards the roots were kept incubated with DPPSC for periodontal differentiation for 21 days.

Periodontal Tissue Differentiation on Tooth Surface

The transversal sections of the teeth were placed in 6 well culture plates, the DPPSC were seeded at 20000 cells per well in 4 ml of osteogenic medium and incubated at 37° C. for 3 weeks. The osteogenic medium consists of α-MEM (Gibco) containing 10% heat-inactivated FBS (Biochrom), 10 mM β-glycerol phosphate (Sigma-Aldrich), 50 µM L ascorbic acid (Sigma-Aldrich), 0.01 µM dexamethasone and 1× penicillin/streptomycin solution. Medium was changed every 3 days over a period of 21 days.

Scanning Electron Microscopy Analysis

After 3 weeks of co-culturing the cells, teeth sheets were processed for SEM. Samples were fixed with 2.5% glutaraldehyde (Ted Pella Inc.) in 0.1 M Na-ca codylate buffer EMS, Electron Microscopy Sciences, Hatfield, Pa.) (pH 7.2) for 1 hour on ice. After fixation, samples were treated with 1% osmium tetroxide (OsO4) for 1 hour. The samples were then dehydrated in serial solutions of acetone (30-100%) with the scaffolds mounted on aluminium stubs. The samples were examined with a Zeiss 940 DSM scanning electron microscope.

Histological Analysis

Teeth that were cultured for 21 days, were fixed with 10% formalin for 24 hours, and then carried to the Pathology Anatomy department of the Instituto Universitario Dexeus (Barcelona, Spain). The harvested samples were embedded in paraffin, and cut into 4-µm-thick sections. The sections were stained with Haematoxylin and eosin (H&E), Alcian blue and Masson's trichrome to determine the formation of new collagen fibers, blood vessels and cementoblast-like cells. An image analysis system was used (Image-Pro Plus™, Media Cybernetic, SilverSprings, Md.).

Results

Cell Culture of DPPSC/Periodontal Tissue Differentiation

Figure 14:
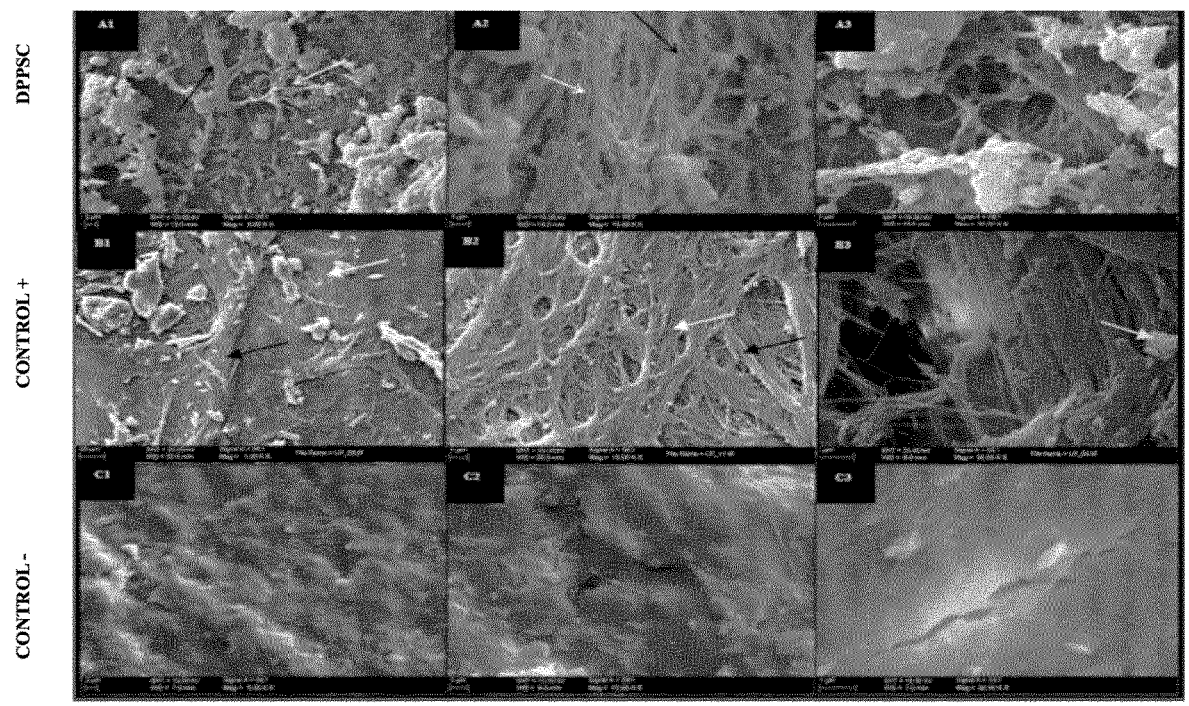
FIG. 14. SEM of 3D differentiation of DPPSCs at P4 using a human dental root scaffold for 21 days into periodontal tissues. DPPSC group (A1, A2, A3) treated surface with BBL. After 3 weeks of differentiation, collagen fibers (white arrows), some blood vessels (black arrows), fibrous tissue and some cemento blast-like cells (yellow arrow) was produced in the sample. Control group (B1, B2, B3) human periodontal tissue in different augmentations (5000×, 15000× and 30000×). Control group (C1,C2,C3) where is not shown the presence of cells or tissues. This figure is related to Example 7.

After the cells were cultured in vitro for 21 days, the cell-seeded scaffolds were subjected to scanning electron microscopic (SEM) examination. SEM in different augmentations (5000×, 15000× and 30000×) in roots with cement showed a high-density cell mass on the surface of the root for all the samples of DPPSC (FIG. 14 A1, A2, A3), indicating that the cells adhered and grew favorably. After 3 weeks of differentiation, SEM allowed high resolution imaging of the fibrous tissue integration of collagen fibrils with the root matrices. Some blood vessels and some cementoblast-like cells were produced in the samples of DPPSC group treated with BBL which compared with positive control (human periodontal tissue) (FIG. 14 B1, B2, B3), and with negative control (teeth surface without periodontal ligament) (FIG. 14 C1, C2, C3), where there were no presence of cells nor tissues.

Histological Evaluation of Tooth Roots

Figure 15:
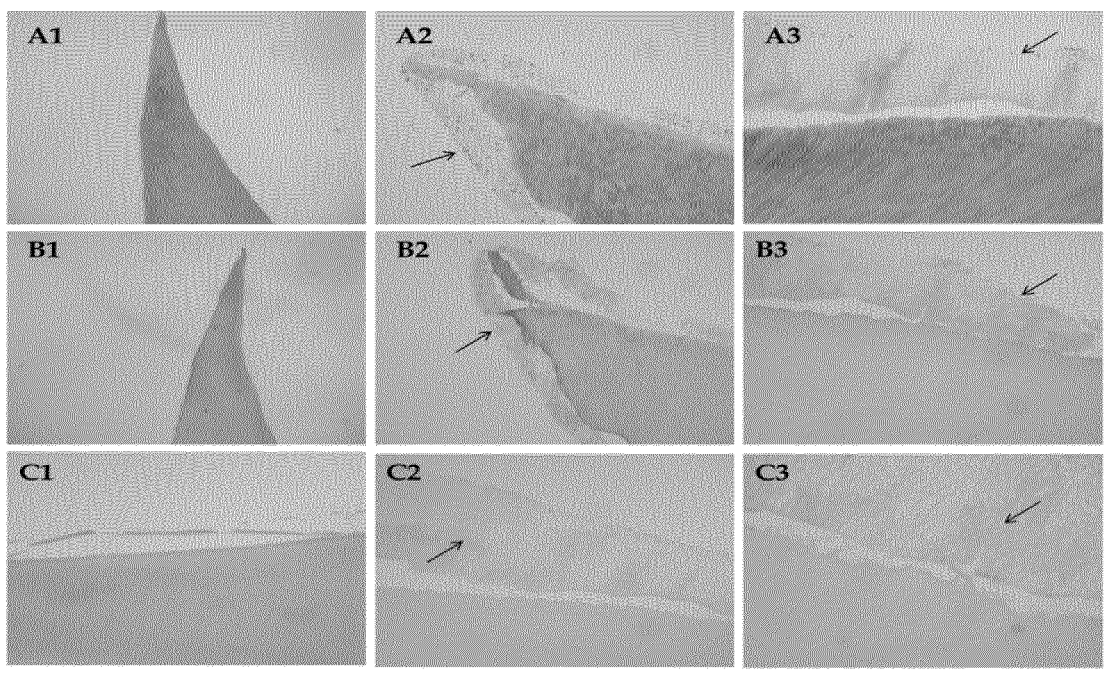
FIG. 15. Histological analysis sections of the DPPSC group (A2-3; B2-3; C2-3) comparing with the control group (A1, B1, C1) with 3 different dyes: Masson's trichrome stain (A1, A2, A3); alcian blue (B1,B2,B3) and Haematoxylin and eosin (H&E) (C1, C2, C3). The DPPSC group (A2-3; B2-3; C2-3) showed the formation of collagen fibers (black arrows) inserted perpendicularly into the cementum-like tissues, which resembled Sharpey's fibers in contrast to the controls (A1, B1, C1). This figure is related to Example 7.

Histological analysis using nuclear staining of non-decalcified sections further supported the SEM findings. In order to visualize early formation of cell clusters, Masson's trichrome stain (FIG. 15 A1, A2, A3); Alcian blue (FIG. 15, B1, B2, B3) and Haematoxylin and eosin (H&E) (FIG. 15 C1, C2, C3) staining were employed. Histological section of the group DPPSC (FIG. 15 A2-3; B2-3; C2-3) showed the formation of collagen fibers inserted perpendicularly into the cementum-like tissues, which resembled Sharpey's fibres in contrast to the control group (FIG. 15 A1, B1, C1). Higher magnification (FIG. 15 A3, B3, C3) revealed the homogeneity of the newly formed reparative collagen fibres that attached well onto the surfaces at 21 days.

The experimental results show, due to the use of the bone bioactive composition, an improved calcification of the cementoblast-like cells together with a recuperation of the collagen fibrils of the periodontal ligament, which is the major defect in periodontitis.

BIBLIOGRAPHIC REFERENCES

Patent Literature

US20070213832 (Wen Hai B)

Non-Patent Literature

Albrektsson T, et al. "Osseointegrated titanium implants Requirements for ensuring a long-lasting, direct bone-to-implant anchorage in man" Acta Orthop Scand 1981, 52:155-170

Anselme K "Osteoblast adhesion on biomaterials" Biomaterials 2000, 21:667

Galler K M, et al. "Bioengineering of dental stem cells in a PEGylated fibrin gel" Regen Med. 2011, 6(2):191-200

García A J "Get a grip: integrins in cell-biomaterial interactions" Biomaterials 2005, 26:7525

Howlett C R, et al. "Mechanism of initial attachment of cells derived from human bone to commonly used prosthetic materials during cell culture" Biomaterials 1994, 15:213

Kilpadi K L, et al. "Hydroxylapatite binds more serum proteins, purified integrins, and osteoblast precursor cells than titanium or steel" J Biomed Mater Res 2001, 57:258

Lindahl C. "Biomimetic deposition of hydroxyapatite on titanium implant materials" Uppsala Univ. 1 Jan. 2012, pages 978-91

Lindberg F. et al., "Hydrohylapatite growth onf single crystal rutile substrates" Biomaterials, Elsevier Science Publishers BV, Barking G B, vol. 29, no 23, 1 Aug. 2008 pages 3317-23

Mohan S, et al. "Bone growth factors" Clin Orthop Relat Res 1991, 263:30-48

Scotchford C A, et al. "Chemically patterned, metal-oxide-based surfaces produced by photolithographic techniques for studying protein- and cell-interactions. II: Protein adsorption and early cell interactions" Biomaterials 2003, 24:1147

Sheikh Z, et al. "Natural graft tissues and synthetic biomaterials for periodontal and alveolar bone reconstructive applications: a review" Biomater Res. 2017; 21.9.

Steele J G, et al. "Attachment of human bone cells to tissue culture polystyrene and to unmodified polystyrene: the effect of surface chemistry upon initial cell attachment" J Biomater Sci Polym Ed 1993, 5:245

Urist M R, et al. "Bone cell differentiation and growth factors" Science 1983, 220:680-686

Wozney J M, et al. "Growth factors influencing bone development" J Cell Sci Suppl 1990, 13:149-156

Yang J et al. "Effects of oestrogen deficiency on rat mandibular and tibial microarchitecture" Dentomaxillofac Radiol 2003 July, 32(4):247-51

The invention claimed is:

1. A method for promoting osteogenesis, the method comprising:
   (a) when the osteogenesis is promoted in an implant: submerging the implant in a bone bioactive composition comprising a water based salt solution comprising disodium hydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, and potassium chloride in a concentration from 2.3 to 3.1 mM in the solution, wherein the pH of the solution is between 7.0 and 7.6,
   and directly inserting the implant into the bone of a subject in need; and
   (b) when the osteogenesis is promoted in a subject in need thereof, administering an effective amount of a bone bioactive composition comprising a water-based salt solution comprising disodium hydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, and potassium chloride in a concentration from 2.3 to 3.1 mM in the solution, to a subject in need thereof, wherein the pH of the solution is between 7.0 and 7.6;
   wherein the bone bioactive composition in (a) and (b) does not comprise a growth factor; and
   wherein the water-based salt solution of the bone bioactive composition in (a) and (b) is the promoter of the osteogenesis.

2. The method according to claim 1, wherein the solution further comprises a calcium salt and a salt of a divalent metal different from calcium.

3. The method according to claim 2, wherein the calcium salt is in a concentration from 7 to 15 mM in the solution and the salt of a divalent metal different from calcium is in a concentration from 2 to 12 mM in the solution.

4. The method according to claim 2, wherein the calcium salt is calcium chloride and the salt of a divalent metal different from calcium is magnesium chloride.

5. The method according to claim 1, wherein the solution further comprises a chelating agent.

6. The method according to claim 5, wherein the chelating agent is EDTA.

7. The method according to claim 1, wherein the pH of the solution is between 7.4 and 7.6.

8. The method according to claim 7, wherein the pH of the solution is 7.6.

9. The method according to claim 1, wherein the implant is a dental titanium implant.

10. A bone bioactive composition comprising a water-based salt solution comprising disodium hydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, potassium chloride in a concentration from 2.3 to 3.1 mM in the solution, a calcium salt in a concentration from 7 to 15 mM in the solution, a salt of a divalent metal different from calcium in a concentration from 2 to 12 mM in the solution, and a chelating agent, wherein the pH of the solution is between 7.0 and 7.6.

11. The bone bioactive composition according to claim 10, wherein the calcium salt is calcium chloride and the salt of a divalent metal different from calcium is magnesium chloride.

12. The bone bioactive composition according to claim 11, comprising 10 mM disodium hydrogen phosphate, 137 mM sodium chloride, 1.8 mM potassium hydrogen phosphate, 2.7 mM potassium chloride, 8.4 mM magnesium chloride, 10.81 mM calcium chloride, and 68.4 mM EDTA.

13. The bone bioactive composition according to claim 10, wherein the water-based salt solution is prepared using solid forms of the following: the disodium hydrogen phosphate, the sodium chloride, the potassium hydrogen phosphate, the potassium chloride, the calcium salt, the salt of a divalent metal different from calcium, and the chelating agent.

14. A kit comprising the bone bioactive composition as defined in claim 10 and an implant.

15. A method for promoting osteogenesis, the method comprising administering an effective amount of a bone bioactive composition according to claim 10 to a subject in need thereof.

16. A method for promoting osteogenesis, the method comprising:
(a) when the osteogenesis is promoted in an implant:
submerging the implant in a bone bioactive composition comprising a water based salt solution comprising disodium hydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, and potassium chloride in a concentration from 2.3 to 3.1 mM in the solution, wherein the pH of the solution is between 7.0 and 7.6,
and directly inserting the implant into the bone of a subject in need; and
(b) when the osteogenesis is promoted in a subject in need thereof, administering an effective amount of a bone bioactive composition comprising a water-based salt solution comprising disodium hydrogen phosphate in a concentration from 8 to 12 mM in the solution, sodium chloride in a concentration from 130 to 140 mM in the solution, potassium hydrogen phosphate in a concentration from 1.4 to 2.2 mM in the solution, and potassium chloride in a concentration from 2.3 to 3.1 mM in the solution, to a subject in need thereof, wherein the pH of the solution is between 7.0 and 7.6; and
wherein the water-based salt solution of the bone bioactive composition in (a) and (b) is the promoter of the osteogenesis; and
wherein the bone active composition does not comprise a further ingredient which promotes osteogenesis.

17. The method of claim 16, wherein the solution further comprises a calcium salt and a salt of a divalent metal different from calcium.

18. The method of claim 16, wherein the solution further comprises a chelating agent.

19. The method according to claim 16, wherein the pH of the solution is between 7.4 and 7.6.

20. The method according to claim 16, wherein the implant is a dental titanium implant.

* * * * *